United States Patent [19]

Fox et al.

[11] Patent Number: 5,246,924

[45] Date of Patent: Sep. 21, 1993

[54] METHOD FOR TREATING HEPATITIS B VIRUS INFECTIONS USING 1-(2'-DEOXY-2'-FLUORO-BETA-D-ARABINOFURANOSYL)-5-ETHYLURACIL

[75] Inventors: Jack J. Fox, White Plains; Kyoichi A. Watanabe, Portchester, both of N.Y.; Carlos Lopez, Carmel, Ind.; Christian G. Trepo, Bran, France

[73] Assignees: Sloan-Kettering Institute for Cancer Research, New York, N.Y.; Institut National de la Sante et de la Recherche Medicale, Paris, France

[21] Appl. No.: 700,334

[22] Filed: May 6, 1991

Related U.S. Application Data

[63] Continuation of Ser. No. 318,602, Mar. 3, 1989, abandoned, which is a continuation-in-part of Ser. No. 92,446, Sep. 3, 1987, abandoned.

[30] Foreign Application Priority Data

Sep. 2, 1988 [CA] Canada ................................ 576381

[51] Int. Cl.$^5$ .............................................. A61K 31/70
[52] U.S. Cl. ......................................... 514/50; 514/49; 514/885; 536/28.54
[58] Field of Search .................... 536/23; 514/49, 50, 514/45

[56] References Cited

U.S. PATENT DOCUMENTS 4,093,714  6/1978  Tolman et al. ........................ 514/48
4,828,830  5/1989  Wong ..................................... 514/2

OTHER PUBLICATIONS

Fox, J. et al. "Antiviral activities of some newer 2'-fluoro-5-substituted arabinosylpyrimidine nucleosides", Int. Congr. Ser.-Excerpta Med. 1985, Chem. Abstr. 104(7) 45345y.

Colacino et al., Antimicrobial Agents and Chemotherapy, Oct. 1983 pp. 505–508.

T-C. Chou, et al. (1981), Cancer Res. 41: 3336–3342.

C. W. Young, et al. (1983), Cancer Res. 43: 5006–5009.

B. Leyland-Jones, et al. (1986), Infectious Dis. 154: 430–436.

R. F. Schinazi, et al. (1983), Antimicrobial Agents Chemother 24: 95–103.

T-C. Chou, et al. (1985), Proceedings of AACR 26: 333.

Y-C. Cheng, et al. (1981), Antimicrobial Agents Chemother 20: 420–423.

C. Lopez, et al. (1980), Antimicrobial Agents Chemother 17: 803–806.

H. Machida, et al. (1982), Antimicrobial Agents Chemother 21: 358–361.

K. F. Soike, et al. (1986), Antimicrobial Agents Chemother 29: 20–25.

B. S. Blumberg, et al. (1981), Hum. Pathol. 12: 1107–1113.

O. Hantz, et al. (1984), Antimicrobial Agents Chemother 25: 242–246.

O. Hantz, et al. (1984), Antiviral Res. 4: 187–199.

J. A. Coderre, et al. (1983), J. Med. Chem. 26: 1149–1152.

M. E. Perlman, et al. (1985), J. Med. Chem. 28: 741–748.

M. M. Mansuri, et al. (1987), J. Med. Chem. 30: 867–871.

*Primary Examiner*—Johnnie R. Brown
*Assistant Examiner*—James O. Wilson
*Attorney, Agent, or Firm*—John P. White

[57] ABSTRACT

The present invention relates to a composition for, and a method of, treating a hepatitis viral infection in a subject using 1-(2'-deoxy-2'-fluoro-beta-D-arabinofuranosyl)-5-ethyluracil [FEAU].

4 Claims, 14 Drawing Sheets

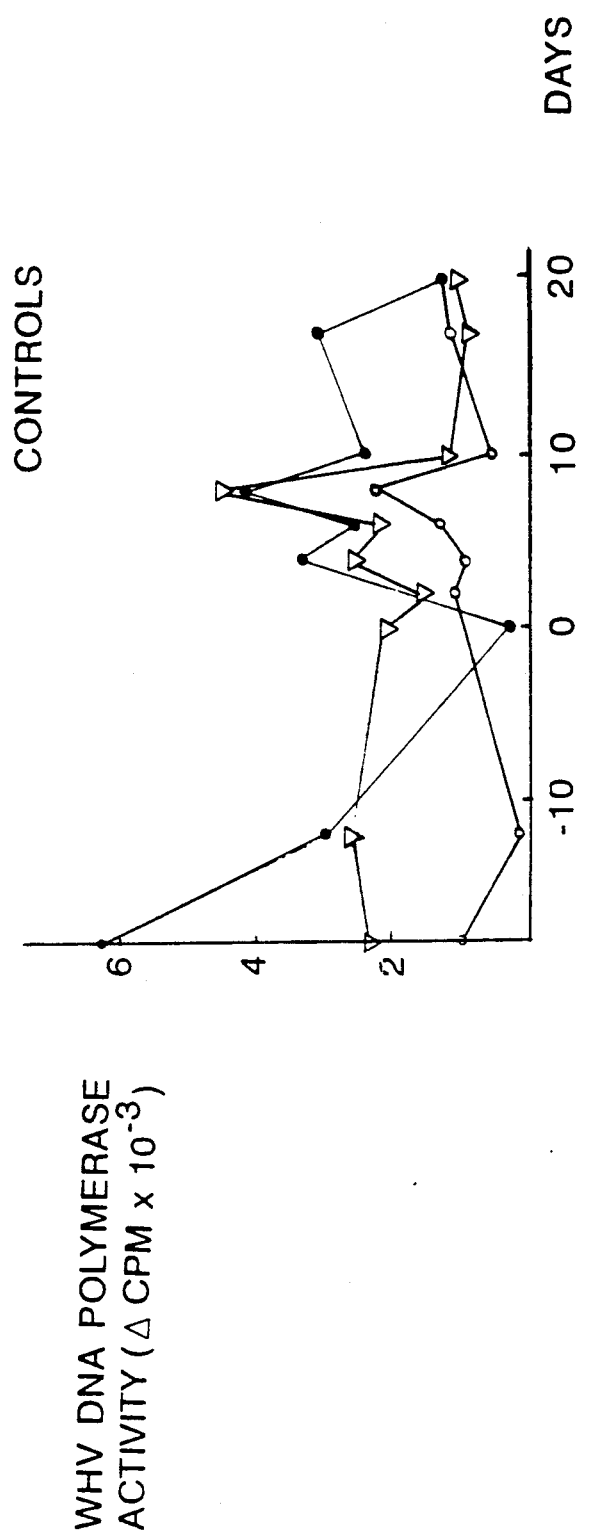

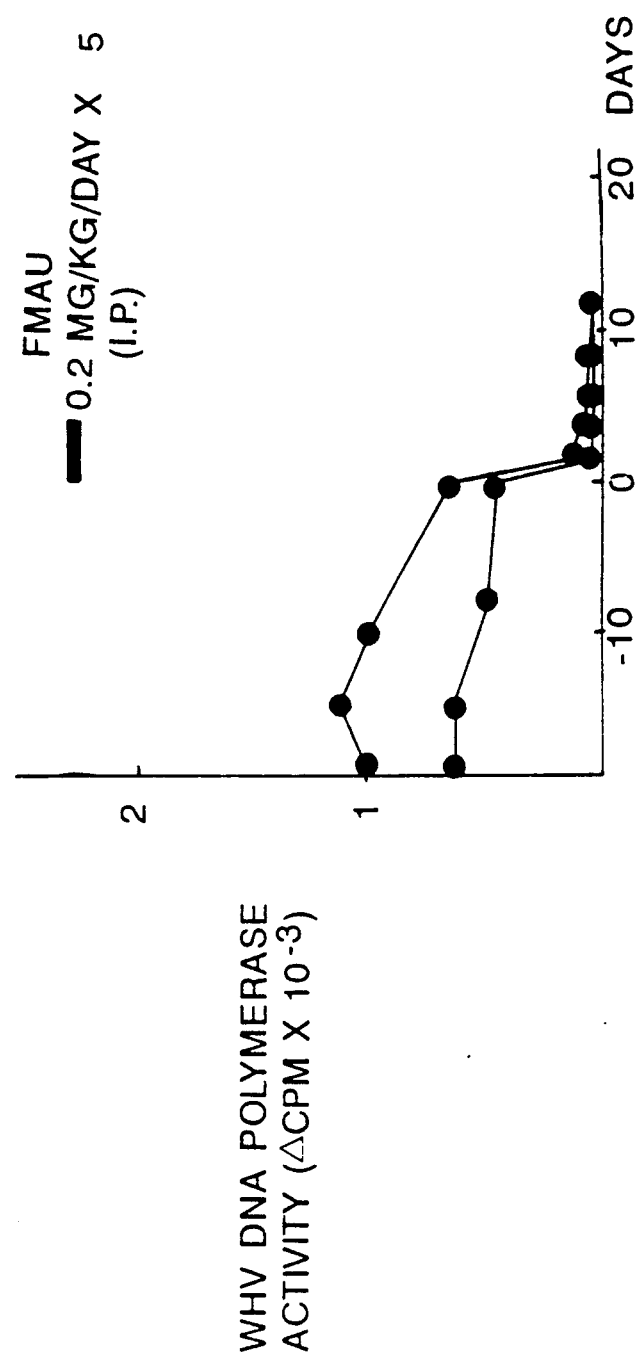

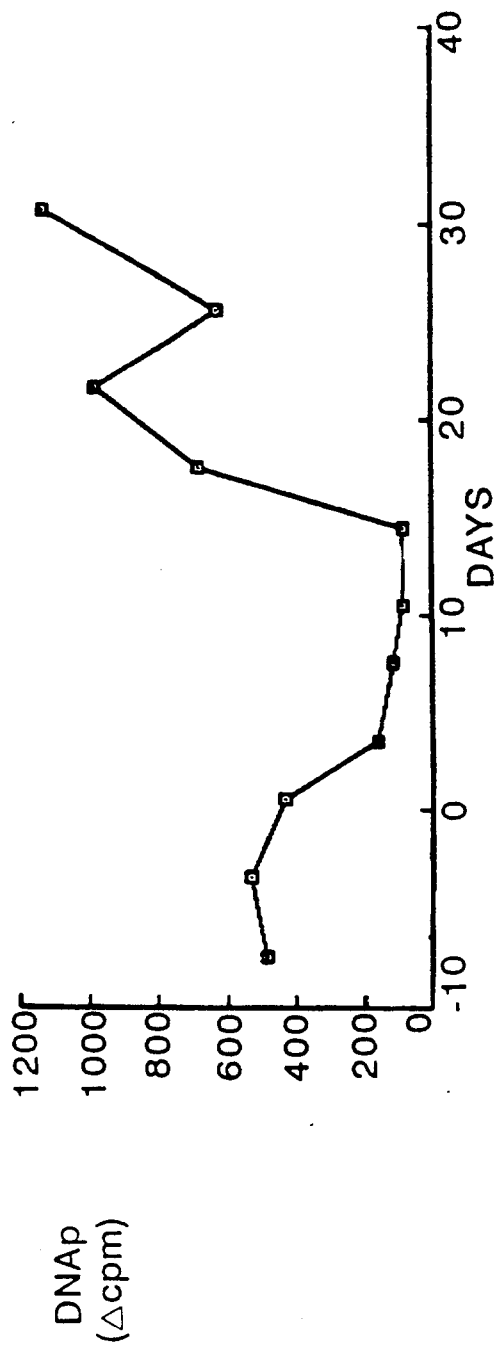

METHOD FOR TREATING HEPATITIS B VIRUS INFECTIONS USING 1-(2'-DEOXY-2'-FLUORO-BETA-D-ARABINOFURANOSYL)-5-ETHYLURACIL

The present invention was partially funded by the National Cancer Institute under Grants Nos. CA-08748, 18601, and 18856, by CA-44094, Department of Health and Human Services, by The Veterans Administration, and by National Institute of Allergy and Infectious Diseases' grant No. NO-A1-62521. Accordingly, the United States Government has certain rights in this invention.

This is a continuation of application Ser. No. 318,602, filed Mar. 3, 1989 now abandoned, which. is a continuation-in-part of U.S. Ser. No. 092,446, filed Sept. 3, 1987, now abandoned, the contents of which are hereby incorporated by reference into the present application.

BACKGROUND OF THE INVENTION

Within this application several publications are referenced by Arabic numerals within parentheses. Full citations for these references may be found at the end of the specification immediately preceding the claims. The disclosures of these publications in their entirety are hereby incorporated by reference into this application in order to more fully describe the state of the art to which this invention pertains.

This invention relates to a composition for, and a method of, treating hepatitis virus infections using 1-(2'-deoxy-2'-fluoro-beta-D-arabino-furanosyl)-5-ethyluracil [FEAU]. FEAU is a member of the family of 5-substituted-1-(2'-deoxy-2'-substituted-beta-D-arabinofuranosyl) compounds, previously known as antiherpes virus agents, disclosed in U.S. Pat. No. 4,211,773 to Lopez et al., but FEAU per se is not disclosed therein. FEAU and its antiherpes activity, however, are disclosed in Fox et al. in *Herpes Viruses and Virus Chemotherapy* (R. Kano, A. Nakajima, eds.) Excerpta Medica, Amsterdam, pp. 53–56 (1985). Other examples of this family of compounds include 1-(2'-deoxy-2'-fluorobeta-D-arabinofuranosyl)-5-methyluracil [FMAU] and 1-(2'-deoxy-2'-fluoro-beta-D-arabinofuranosyl)-5-iodocytosine [FIAC].

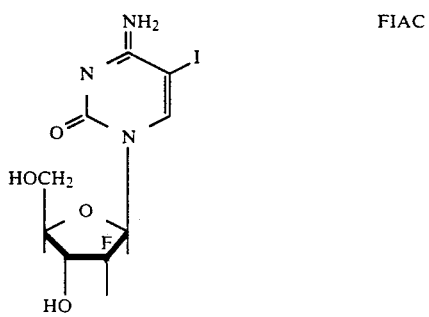

FIAC

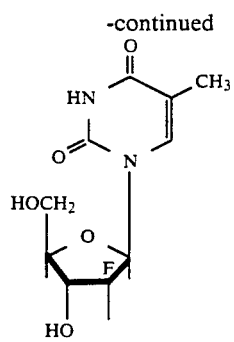

FMAU

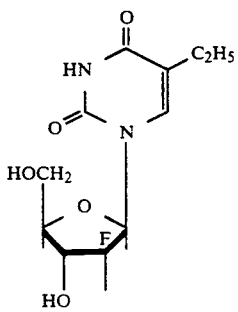

FEAU

Although it would not have been expected that an antiherpes virus agent would also be effective in the treatment of hepatitis, these compounds were investigated for their usefulness as antihepatitis agents. During this investigation, it was found that FEAU was particularly ideal in the treatment of hepatitis. Although FMAU was shown to be as effective or perhaps more effective, at inhibiting replication of the hepatitis virus, it produced potentially lethal, toxic side effects. FEAU, however, was shown to effectively inhibit replication of the hepatitis virus without causing severe, toxic side effects.

One particulary common form of hepatitis is the hepatitis B virion (HBV). HBV, also known as the Dane particle, is a 42 nm complex spherical particle composed of an outer lipoprotein coat (hepatitis B surface antigen, HBsAg) and an inner core (hepatitis B core antigen, HBcAG). This core contains a circular, partially double-stranded DNA and a DNA polymerase. In vitro, the DNA polymerase fills in a large single-stranded region in the genome, generating a fully double-stranded region in the genome.

The specific nature of the Dane particle-associated DNA polymerase is uncertain. Selective inhibition of the HBV DNA polymerase by intercalating agents, pyrophosphate analogs, and arabinofuranosyl nucleotides is known and offers the ability to inhibit hepatitis B virus replication in individuals suffering from chronic hepatitis B.

An agent very closely related to HBV is known in woodchucks: the woodchuck hepatitis virus (WHV). Both viruses belong to the same class of viruses, sometimes designated Hepa-DNA viruses. As previously suggested, HBV and WHV DNA polymerases share the same basic features. The WHV DNA polymerase activity was, therefore, studied in parallel with that of HBV in initial in vitro work.

Of the class of Hepa-DNA viruses, only HBV and WHV are known to cause chronic active hepatitis and hepatocellular carcinoma. Generally, WHV infection in woodchucks mimics the HBV infection in man both virologically and histopathologically.

Evidence linking hepatitis B virus and hepatocellular carcinoma comes from the woodchuck hepatitis virus (WHV)/woodchuck model. It is possible to induce hepatocellular carcinoma experimentally in the woodchuck by inoculation with WHV at birth. These data not only provide experimental support for the cancer causing role of WHV but they further validate the use of the woodchuck hepatitis virus as a pathogenic model for the hepatitis B virus in man.

SUMMARY OF THE INVENTION

This invention relates to a composition for treating a hepatitis virus infection in a subject comprising an amount of the compound 1-(2'-deoxy-2'-fluoro-beta-D-arabinofuranosyl)-5-ethyluracil, having the structure:

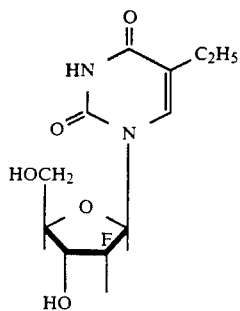

and prodrug forms and pharmaceutically acceptable salts thereof, effective to inhibit replication of the hepatitis virus in the subject and a pharmaceutically acceptable carrier.

This invention also provides a method for treating a hepatitis virus infection in a subject comprising administering to the subject an amount of the compound having the structure:

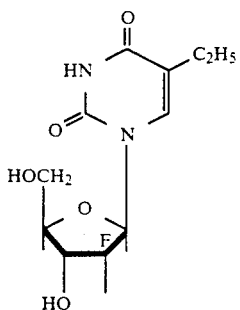

and prodrug forms and pharmaceutically acceptable salts thereof, effective to inhibit replication of the hepatitis virus in the subject.

BRIEF DESCRIPTION OF THE FIGURES

FIG. 1 illustrates WHV DNA polymerase activity in chronically infected woodchucks.

FIGS. 5A to 5E illustrate serum levels of WHV DNA and polymerase activity in treated woodchucks:
5(A)=control
5(B)=FMAU
5(C)=FIAC
5(D)=are AMP
5(E)=FEAU.

DETAILED DESCRIPTION OF THE INVENTION

Figure 2A:
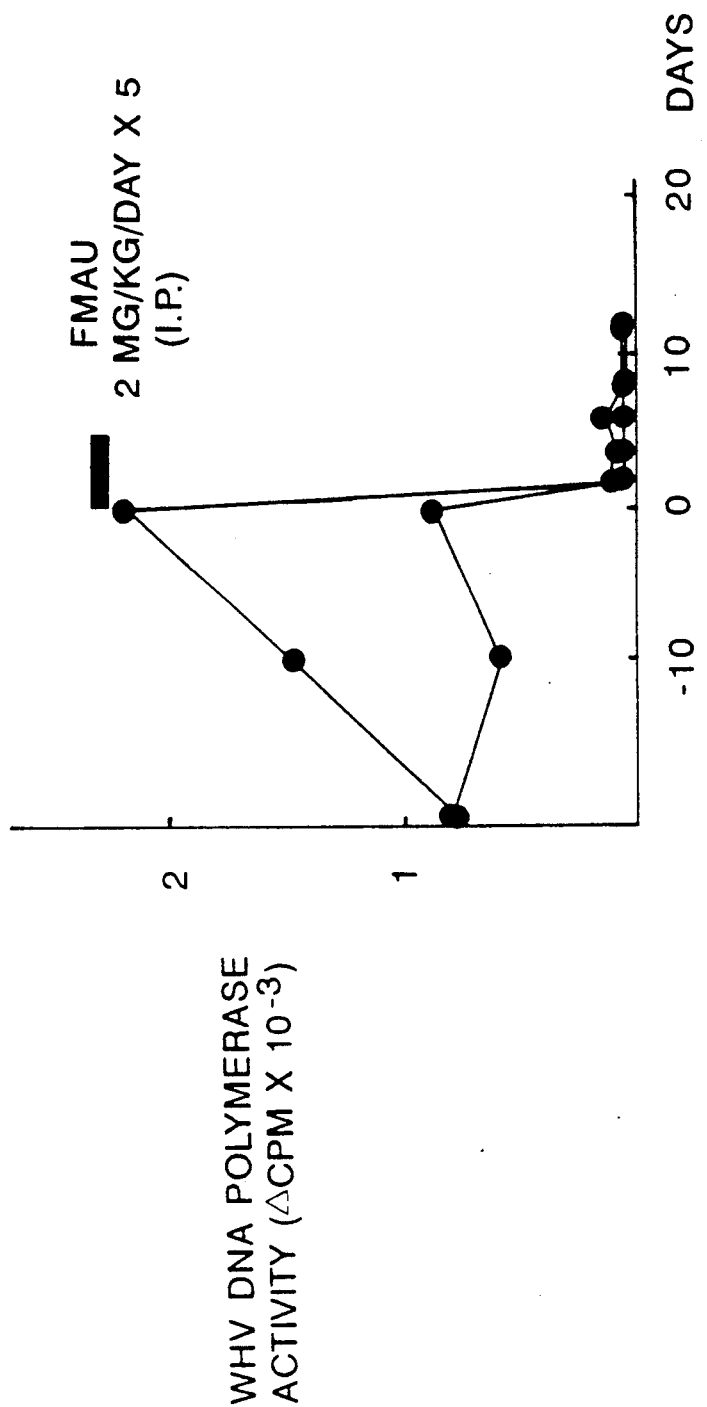
FIG. 2 is a comparison of the inhibition of WHV replication in woodchucks treated with FMAU (FIG. 2A) and FEAU (FIG. 2B).

The present invention provides a composition for treating a hepatitis virus infection in a subject, particularly a human being, comprising an amount of the compound 1-(2'-deoxy-2'-fluoro-beta-D-arabinofuranosyl)-5-ethyluracil [FEAU] having the structure:

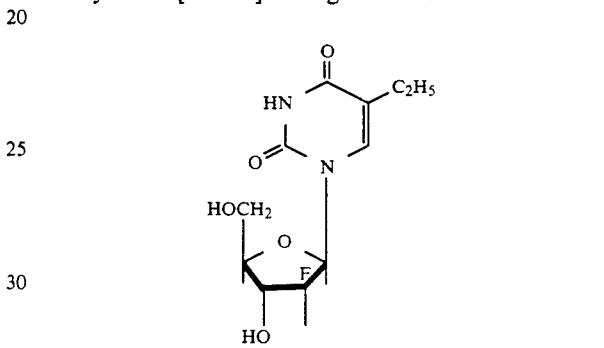

and prodrug forms and pharmaceutically acceptable salts thereof, effective to inhibit replication of the hepatitis virus in the subject and a pharmaceutically-acceptable carrier.

As used herein, the term "prodrug forms" encompasses any chemical entity which upon administration to a subject may be readily converted to FEAU. Merely by way of example, prodrug forms of FEAU include those in which the hydroxyl group at the 5' position on the sugar is converted to a mono- or di-phosphate group. As used herein, the term "pharmaceutically acceptable salt" encompasses any conventional salt of FEAU which may be employed in lieu of FEAU such as any of the alkali or alkaline metal salts of FEAU. Finally, as used herein, the term "pharmaceutically acceptable carrier" encompasses any of the standard pharmaceutical carriers such as sterile solutions, tablets, coated tablets and capsules. Typically such carriers contain excipients such as starch, milk, sugar, certain types of clay, gelatin, stearic acid or salts thereof, magnesium or calcium stearate, talc, vegetable fats or oils, gums, glycols, or other known excipients. Such carriers may also include flavor and color additives or other ingredients. Compositions comprising such carriers are formulated by well known, conventional methods. In a presently preferred embodiment, the composition is one adapted for oral administration.

In accordance with the teaching of this invention, the hepatitis virus may be the hepatitis A, hepatitis B, or hepatitis non-A, non-B virus, particularly the hepatitis B virus.

Also, in accordance with the teachings of this invention, the amount of the compound incorporated in the composition may vary widely. Methods for determining the precise amount are well known to those skilled in the art and depend inter alia upon the subject to be treated, the specific pharmaceutical carrier and route of administration being employed, and the frequency with which the composition is to be administered. In general, the amount of the compound in the composition effective to inhibit replication of the hepatitis virus is from about 0.01 mg/kg body weight of the subject/day up to about 100.0 mg/kg body weight of the subject/day. Preferably, the amount is greater than about 0.04 mg/kg body weight of the subject/day, for example, about 0.04 to about 50.0 mg/kg body weight of the subject/day.

The present invention also provides a method for treating a hepatitis virus infection in a subject comprising administering to the subject an amount of the compound having the structure:

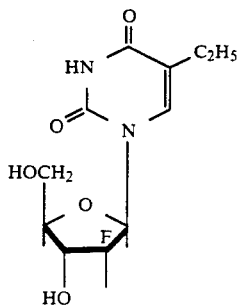

and prodrug forms and pharmaceutically acceptable salts thereof, effective to inhibit replication of the hepatitis virus in the subject.

In this method, the administration of the compound may be effected by any of the well known methods, including but not limited to oral, intravenous, intramuscular, and subcutaneous administration. Preferably, the compound is administered orally.

In the practive of the method of this invention the amount of the compound effective to inhibit replication of the virus is as in the composition, that is, generally from about 0.01 mg/kg body weight of the subject/day up to about 100.00 mg/kg body weight of the subject/day, preferably greater than about 0.04 mg/kg body weight of the subject/day, for example, about 0.04 to about 50.0 mg/kg body weight of the subject/day.

Finally, the hepatitis virus which may be treated using the method may be hepatitis A, hepatitis B, or hepatitis non-A, non-B virus, particularly hepatitis B.

EXPERIMENTAL DETAILS

The examples which follow are set forth to aid in an understanding of the invention, but are not intended to, and should not be construed so as to, limit in any way the invention as defined by the claims which follow.

MATERIALS AND METHODS

IN VITRO TESTING

Preparation of Virus Particles

HBV particles containing DNA polymerase activity were purified from the serum of an immunosuppressed patient, positive for HBsAG. WHV was obtained from a serum pool of five woodchucks (*Marmota monax*), chronic carriers of the virus. The woodchucks initially imported from Pennsylvania belonged to a colony followed for over one year by serological tests as reported in Hantz et al., J. Virol. Metho. 7: 45–55 (1983). Virus was purified by centrifugation on sucrose and isopycnic CsCl gradients.

Chemicals

For in vitro testing, triphosphates were used. The use of triphosphates is required because of expected cell metabolism processes.

Unlabeled nucleoside triphosphates were obtained from Sigma Chemical Company, St. Louis, Mo., U.S.A. Tritiated deoxyribonucleoside triphosphates, [$^3$H] dTTP (30 Ci/mmol), [$^3$H] dATP (24 Ci/mmol), [$^3$H] dCTP (17 Ci/mmol) and [$^3$H] dCTP (9,5 Ci/mmol), were obtained from Amersham (Amershal, France). ACV was obtained from Burroughs Welcome, Chapel Hill, N.C.; and the synthesis of BVdU is described by de Clerq et al., Proc. Natl. Acad. Sci. U.S.A. 76: 2947–2951 (1979). FIAC synthesis is described in Lopez et al. (U.S. Pat. No. 4,211,773). The synthesis of FEAU is described in Watanabe et al., J. Med. Chem. 27: 91–94 (1984). All three nucleoside analogs were converted to their corresponding 5'-triphosphates by a procedure described by Allaudeen et al., Proc. Natl. Acad. Sci. U.S.A. 78: 2698–2702 (1981). The purity of the triphosphates was examined by $^1$H NMR on a Bruker HX-270 spectrometer and by high pressure liquid chromatography on an Altex Model 332 gradient liquid chromatograph.

DNA Polymerase Assay

DNA polymerase was assayed as described by Kaplan et al., J. Virol. 12: 995 (1973) with minor modification. The assay was performed in a 50 $\mu$l reaction mixture containing 50 mM Tris-HCl pH 7.5, 40 mM MgCl$_2$, 60 mM NH$_4$Cl, 100 $\mu$M each dATP, dCTP and dGTP, 0.2–0.7 $\mu$M [$^3$H] dTTP (30 Ci/mmol), 10 mM 2-mercaptoethanol, 0.5% Nonidet P-40 and enzyme. The reaction was started by addition of the virus particles with 2-mercaptoethanol and Nonidet P 40. Incubation was at 37° C. for 1 hour. Acid insoluble radioactive material was collected on a glass fiber filter (GF/C Whatman). Filters were washed 5 times with cold 5% trichloracetic acid containing 10 mM sodium pyrophosphate, then with 95% ethanol. Radioactivity of the dried filter was measured in a liquid scintillation counter.

Agarose Gel Electrophoresis of [$^{32}$p] DNA

The [$^{32}$p] DNA product of the endogenous DNA polymerase reaction was analyzed by agarose gel electrophoresis as described by Summers et al., Proc. Natl. Acad. Sci. U.S.A. 72: 4597–4601 (1975). The reaction was made in 15 $\mu$l of the standard DNA polymerase mixture with 1 $\mu$M [$^{32}$p] dCTP (500 Ci/mmol) as labeled nucleotide.

After 2 hours incubation at 37° C., the reaction was terminated by the addition of 20 $\mu$l of 10 mM Tris, 10 mM EDTA, 0.1 mg per ml of proteinase K, 0.1% (wt/vol) sodium dodecyl sulfate, followed by further incubation for 60 mn at 37° C. Five (5) $\mu$l of 5% (wt/vol) sucrose, 1% bromophenol blue was added, the entire mixture was heated for 60 mn at 65° C., immediately cooled at 4° C. and then analyzed by electrophoresis on a horizontal slab gel of 1% agarose. After electrophoresis, the gel was dried and developed by autoradiography.

Product of HBV and WHV DNA Polymerase Reaction

The specificity and the efficiency of the DNA polymerase in the HBV and WHV particle preparations were controlled by analysis of the labeled DNA synthesized during the endogenous reaction. The DNA polymerase assay was made as described under methods and materials with [$^{32}$p] dCTP as labeled nucleotide. The product of the reaction was then analyzed by agarose gel electrophoresis and autoradiography. The results showed the progressive synthesis of HBV and WHV DNA after 15, 30, 120, and 180 mn of reaction. For HBV, a complete 3.3 kb long DNA and smaller forms (from 1.8 to 2.8 kb) corresponding to an incomplete filling of the single-stranded region of the viral genome were obtained. The product of the WHV DNA polymerase reaction was more heterogeneous and migrated slightly faster; after 180 mn of the reaction the longer form of WHV DNA was 3.1 kb long.

Relative Sensitivities of HBV and WHV DNA Polymerases to ACVTP, FIACTP and BVdUTP The relative sensitivities of both enzymes to ACVTP, FIACTP and BVdUTP were compared using an excess of nucleotides. For each inhibitor, the concentration of the corresponding radioactive triphosphate was maintained at 2 to 3 times the Km value while the remaining nucleotides were in great excess (50 $\mu$M). Results show that FIACTP was the most efficient inhibitor of HBV DNA polymerase and ara-CTP was the least efficient; BVdUTP and ara-TTP showed a similar inhibition.

Similar results were observed with WHV DNA polymerase. The concentrations of triphosphates required to inhibit 50% of HBV and WHV DNA polymerases were determined and it was shown that ID$_{50}$ of FIACTP was very low (0.5 $\mu$M) compared with the values obtained for BVdUTP and ACVTP which were 5 and 18 times more, respectively.

Kinetics of Inhibition

Although the mode of action for the various compounds is known to be different, the nature of ACVTP, FIACTP and BVdUTP inhibition of viral DNA synthesis catalyzed by HBV and WHV DNA polymerases was examined by determining the extent of inhibition with increasing concentrations of the substrates. In assays with ACVTP, [$^3$H] dGTP was the rate limiting substrate while the other three nucleotides were in excess. The same conditions were used with [$^3$H] dGTP for FIACTP and [$^3$H] dTTP for BVdUTP inhibition. Lineweaver-Burk plots show that the inhibition of HBV DNA polymerase reaction by ACVTP, FIACTP and BVdUTP was competitive with dGTP, dCTP and dTTP, respectively. Similar results were obtained for WHV DNA polymerase. The Km values of dGTP, dCTP, dTTP and the Ki value of ACVTP and BVdUTP for the DNA polymerases of both viruses were determined. WHV DNA polymerase showed a lower affinity to ACVTP, FIACTP and BVdUTP than HBV DNA polymerase; however, the Km/Ki ratios were comparable for both enzymes.

Effect of BVdUTP, FIACTP and ACVTP on DNA Synthesis In Vitro

To determine the effect of the three analogs on viral DNA synthesis, a time course experiment was performed with HBV DNA polymerase. [$^3$H] dATP was used as the labeled substrate. With all four nucleoside triphosphate substrates, the reaction was linear up to 60 mn. When dTTP, dCTP or dGTP was omitted from the reaction mixture, no significant DNA synthesis was observed. The substitution of dTTP by BVdUTP permitted the viral DNA synthesis up to 46% of the control after 3 hours of reaction. This value increased to 67% of the optimal activity after 4 h of reaction. However, in a similar experiment, no significant DNA synthesis was observed with dTTP substituted by ara-TTP.

When such an experiment was performed with FIACTP instead of dCTP a low incorporation of [$^3$H] dAMP was obtained (about 10% of the control after 3 h of reaction) while no significant incorporation was observed when ara-CTP was used instead of dCTP. The substitution of dGTP by ACVTP did not increase the polymerization process as shown by the efficiency of these different analogs to the alternate substrates of HBV and WHV DNA polymerases. BVdUTP was the most efficient alternate substrate for both enzymes. The DNA synthesized with BVdUTP as alternate substrate was analyzed by agarose gel electrophoresis. Only incomplete filling of the single-stranded region of HBV or WHV DNA was obtained with BVdUTP.

The effect of ACVTP on HBV DNA synthesis was also studied in a time course experiment. [$^3$H] dTTP was the labeled substrate. The reaction was initiated without dGTP or with 5 $\mu$m ACVTP instead of dGTP. Under these conditions, no incorporation of [$^3$H] dTMP could be measured. After 120 minutes of reaction, 100 $\mu$M of dGTP was added. In the assay without dGTP only, the addition of dGTP increased DNA synthesis as expected. However, when the assay was first made with 5 $\mu$M ACVTP instead of dGTP, no DNA synthesis was observed after addition of 100 $\mu$m dGTP. By comparison, when the reaction was started with the same proportion of ACVTP (5 $\mu$M) and dGTP (100 $\mu$M) a significant DNA synthesis was observed. Similar experiments were carried out with ara-ATP and ara-CTP. In both cases, the addition of normal substrate (dATP and dCTP) after 120 mn of reaction in presence of the analog increased the HBV DNA synthesis. Thus, addition of ACVTP instead of the natural triphosphate substrate, dGTP, did not enhance DNA synthesis but seemed to block further elongation.

Inhibitory Effect of the Nucleoside Analogs on HBV and WHV DNA Polymerases

Nucleoside analogs demonstrating antiviral activity have to be converted to their triphosphate derivatives within the cell to interfere with viral DNA synthesis. Preferential inhibition of herpes simplex virus DNA polymerase by ACVTP, BVdUTP and FIACTP have been reported and may explain in part the selective antiviral activity of nucleoside analogs ACV, BVdUTP and FIAC. The in vitro evidence described above, shows that all the three compounds inhibit the DNA polymerases of HBV and WHV and that the inhibition is competitive with the corresponding natural triphosphate substrates. The respective inhibitory activities of ACVTP, BVdUTP, FIACTP and two other nucleotide analogs, ara-CTP and ara-TTP, were compared. Inhibitory activity on HBV and WHV DNA polymerases decreased in the following order: FIACTP, BVdUTP, ara-TTP, ACVTP, Ara-CTP.

IN VIVO TESTING

In vivo Testing of FMAU Against Chronic Active Hepatitis in Woodchucks

The compound FMAU is soluble in water. Therefore, water or water-based solutions are preferred as solvents for administering the compound. The solubility of FMAU is 66 mg/ml at 24° C. and 81 mg/ml at 28° C. Its molecular weight is 260.

All woodchucks bearing chronic active hepatitis virus (Hantz, supra) were administered FMAU twice daily by interperitoneal injections of FMAU in the following dosages:

| No. of Animals | Dosage |
| --- | --- |
| 2 | 2 mg/kg per day for 7 days |
| 2 | 4 mg/kg per day for 5 days |

Dramatic and almost immediate inhibition of woodchuck hepatitis virus replication was observed in all four animals. At the end of one week following dosage administrations, the woodchuck hepatitis virus DNA polymerase had fallen to background levels. FMAU suppressed woodchuck hepatitis virus replication and this inhibition persisted for 20–50 days after cessation of treatment.

Studies were also conducted using acyclovir or ara-AMP in similar dosages. Virus replication levels were diminished. However, these levels rebounded to pretreatment levels soon after cessation of treatment.

Ongoing testing of woodchucks bearing hepatitis virus is being conducted with the following additional pyrimidine nucleoside compounds: FIAC (2'-fluoro-2'-deoxy-arabinosyl-5-iodoocytosine) and FIAU (2'-fluoro-2'-deoxy-arabinosyl-5-iodouracil). As with FMAU, water is the preferred carrier. These compounds are also soluble in water as follows:

|  |  |  | Mol. Wt. |
| --- | --- | --- | --- |
| FIAC | 7.2 mg/l | at 21° C. | 371 |
| FIAU | 4.0 mg/l | at 28° C. | 372 |

If necessary, the solubility of the compounds FMAU, FIAC, and FIAU may be increased by adding acid or base to the aqueous solvent. In this way, FIAC solubility may be increased to about 250 mg/ml by adding about one molar equivalent of hydrochloric acid, although somewhat less concentrated hydrochloric acid will work. For FIAU, the solubility may be increased many fold by adding one equivalent of sodium hydroxide, which makes the sodium salt of FIAU.

EXAMPLE 1

In vivo testing of FEAU

In this example, comparative biochemical and antiviral studies are described for the 2'-fluoro-substituted arabinosylpyrimidine nucleosides, FMAU and FEAU. Biochemical studies indicated that FEAU should be a selective antiherpes virus agent that is less toxic than FMAU. FEAU was evaluated against simian varicella virus infection in African green monkeys and, like FMAU, was highly effective in preventing rash and reducing viremia without apparent toxicity at doses of 30, 10 or 3 mg/kg/day × 10 administered intravenously. Oral administration of FEAU in those monkeys at 10, 3 and 1 mg/kg/day × 10 was equally effective.

FEAU appears to be the most promising of the nucleoside analogs tested thus far against hepa-DNA viruses and, in accordance with the present invention, demonstrates clinical effectiveness against hepatitis B virus.

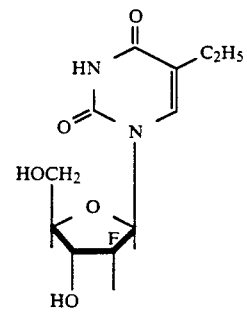

FEAU

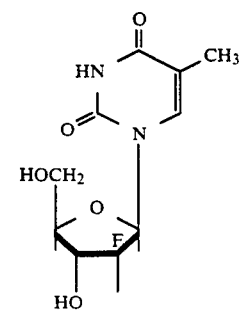

FMAU

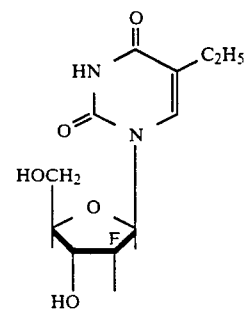

EDU

Since the original report (1) on the synthesis and antiherpes virus activities of several 5-substituted pyrimidine nucleosides bearing the 1-(2'-deoxy-2'-fluoro-beta-D-arabinofuranosyl) moiety, structure-activity studies have indicated that the 2'-fluoro substituent in the "up" (arabino) configuration conferred more potent antiviral activity than did a 2'-OH, hydrogen, or other 2'-halogens (2). Moreover, where studied (3, 4), the 2'-fluoro nucleosides were resistant to catabolic cleavage by nucleoside phosphorylases, presumably a result of the increased metabolic stability of the N-glycosyl linkage imposed by this electronegative 2'-substituent. Of the several 2'-fluoro-5-substituted-arabinosyl pyrimidine nucleosides synthesized (1), FIAC [1-(2'-deoxy-2'-fluorobeta-D-arabinofuranosyl)-5-iodocytosine] has demonstrated clinical efficacy against herpes virus infections in Phase 1 (5) and against varicella zoster virus in Phase 2 (6) clinical trials in immunocompromised cancer patients. The corresponding thymine analog, 1-(2'-deoxy-2'-fluoro-beta-D-arabinofuranosyl)-5-methyluracil [FMAU] was found to be more potent in mice infected with herpes simplex virus (HSV) types 1 and 2 without toxicity at effective dose levels. FMAU was also found to be active in vitro and in vivo against P-815 and L-1210 leukemia cell lines resistant to the antileukemic agent, arabinofuranosylcytosine [Ara-C]. A Phase 1 trial of FMAU in patients with advanced cancer showed that drug-induced central nervous system (CNS) dysfunction was the dose-limiting toxicity (7).

With FMAU as a lead compound, the syntheses of other 5-alkyl substituted 2'-fluoro-ara-uracils were undertaken (8, 9), including 1-(2'-deoxy-2'-fluoro-D-arabinofuranosyl)-5-ethyluracil [FEAU]. As shown in Table I, though FEAU was approximately one log order less potent than FMAU against HSV-1 and HSV-2 infected Vero cells in culture, the former exhibited far less host cell toxicity, resulting in an extremely favorable therapeutic index (9, 10).

is much less effective than FEAU in this HSV-2 mouse encephalitis model. This finding is consistent with a previous observation (1) attesting to the importance of the 2'-fluoro substituent for the anti-HSV activity exhibited by these arabinofuranosyl-pyrimidine nucleosides.

It was concluded previously (11) that FMAU is a most potent and selective antiviral compound for the treatment of mouse encephalitis caused by HSV-2 and therefore deserved consideration as a potential agent in human trials for the treatment of HSV encephalitis in

TABLE I

COMPARATIVE ANTI-HSV ACTIVITY OF FMAU AND FEAU IN PLAQUE REDUCTION ASSAYS IN VERO CELLS

|      | HSV-1 (F)* | | HSV-2 (G)* | | $ID_{50}$ | THER. INDEX $ID_{50}/ED_{90}$ | |
|------|------------|------|------------|------|-----------|-------|-------|
|      | $ED_{50}$ ($\mu$M) | $ED_{90}$ | $ED_{50}$ ($\mu$M) | $ED_{90}$ | ($\mu$M) | HSV-1 | HSV-2 |
| FMAU | 0.010 | 0.042 | 0.023 | 0.09 | 2.8 | 67 | 31 |
| FEAU | 0.024 | 0.26 | 0.24 | 0.91 | 200 | 769 | 220 |

*Correlation Coefficient 0.86.
Cytotoxic effect measured in rapidly dividing cells.

A comparison of the antiviral activity of FMAU, FEAU and 5-ethyl-2'-deoxyuridine (EDU) in mice inoculated intracerebrally with HSV-2 is given in Table II (10). FEAU showed activity at 50 mg/kg/day for 4 days and was highly effective in reducing mortality in these mice at doses of 100-200 mg/kg/day. At these dose levels, no toxicity was observed. In normal (uninfected) mice, FEAU was non-toxic at doses of 800 mg/kg/day given twice daily for 4 days. It is also noteworthy that EDU, which differs structurally from FEAU only by the absence of the 2'-fluoro substituent, neonates and adults at low dose levels. The preliminary data described in Tables I and II for FEAU suggested (10) that this compound may also be worthy of similar consideration. Based upon these earlier findings (10) and on the preliminary biochemical report (12), further comparative biochemical and antiviral studies were undertaken with FMAU and FEAU, including their relative activities against simian varicella virus in the African green monkey and against hepatitis virus in the woodchuck animal model.

TABLE II

ANTIVIRAL EFFECTS OF FEAU, FMAU, AND EDU IN MICE INOCULATED INTRACEREBRALLY WITH HSV-2 (STRAIN G)

| TREATMENT | DOSE* MG/KG/DAY | MDD** | % SURVIVORS | % WT GAIN ON DAY§ | | | |
|---|---|---|---|---|---|---|---|
| | | | | 7 | 14 | 21 | 30 |
| NEG CONTROL (NO VIRUS) | — | | 100 | −3 | 9 | 13 | 16 |
| PBS (VIRUS CONTROL) | 6.7 | | 7 | −22 | −14+ | 8+ | 17+ |
| FEAU | 10 | 9.4 | 8 | | −7 | −13+ 31+ | 36+ |
| | 50 | 11.8 | 25 | 3 | −10 | 16 | 25 |
| | 100 | 11.0 | 72 | 2 | 7 | 13 | 13 |
| | 200 | (14)# | 93 | 0 | 1 | 9 | 13 |

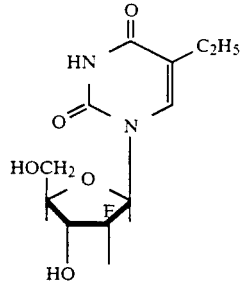

| FMAU | 0.5 | 9.4 | 67 | 1 | 4 | 5 | 7 |

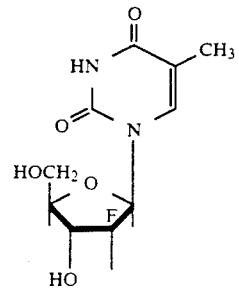

TABLE II-continued
ANTIVIRAL EFFECTS OF FEAU, FMAU, AND EDU IN MICE INOCULATED INTRACEREBRALLY WITH HSV-2 (STRAIN G)

| TREATMENT | DOSE* MG/KG/DAY | MDD** | % SURVIVORS | % WT GAIN ON DAY§ 7 | 14 | 21 | 30 |
|---|---|---|---|---|---|---|---|
| EDU | 800 | 7.6 | 13 | −10 | −6 | 2 | 6 |
|  | 1000 | 8.6 | 33 | 3 | 13 | 34 | 43 |

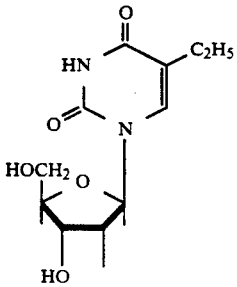

*GIVEN 5 HR AFTER INTRACEREBRAL INOCULATION. DOSE SCHEDULE, TWICE A DAY FOR 4 DAYS.
**CALCULATED ON DAY 21.
NUMBER IN PARENTHESES INDICATE DEATH OF A SINGLE ANIMAL.
§AS COMPARED TO DAY 1.
+BASED ON WT OF A SINGLE SURVIVING ANIMAL ONLY.

Comparative Biochemical Studies

Biochemical studies (13) on the relative effects of FEAU and FMAU on the growth of mammalian cells is shown in Table III. Note that against the human promyelocytic leukemia cell line (HL-60) as well as against Vero cells (derived from the African green monkey), FEAU is far less growth-inhibitory than FMAU, which compares favorably to the in vitro study given in Table I. Similarly against rodent cell lines (p-815, L-1210 and rat bone marrow cells), FEAU is substantially less growth-inhibitory than FMAU (Table II).

Cellular kinetic constants ($K_i$) were determined for the inhibition of natural precursor incorporation into the DNA of L-1210 cells by FEAU and FMAU. Using tritium-labeled natural precursors as substrates (thymidine, 2'-deoxyuridine and 2'-deoxycytidine), it was evident that FEAU was a much weaker inhibitor than FMAU of natural nucleoside anabolism in these mammalian cells (12, 13).

Studies on the incorporation of 2-$^{14}$C-labeled FEAU and FMAU into the DNA of mammalian cells showed very significant differences (Table IV). There was no detectable incorporation of FEAU radioactivity into the DNA of either L-1210 or Vero cell lines, but substantial amounts of FMAU radioactivity were incorporated into the DNA of both cell lines. When HSV-1 infected Vero cells were exposed to $^{14}$C-labeled FEAU and FMAU, both nucleosides incorporated into the DNA of these virus-infected cells. Under these conditions, FMAU incorporation into HSV-1-infected Vero cells is seven-fold greater than that observed for FEAU. This difference in incorporation may be due to the greater affinity of FMAU for viral-encoded DNA polymerase and is comparable to the magnitude of the difference of their anti-herpetic effects in vitro (13).

TABLE III
COMPARISON OF EFFECTS OF FEAU AND FMAU IN MAMMALIAN CELLS

|  | FEAU | FMAU | FEAU/FMAU |
|---|---|---|---|
| ED$_{50}$ (IN μM) FOR INHIBITING CELL GROWTH IN: |  |  |  |
| HL-60 CELLS | 2060 | 15.4 | 133 |
| VERO CELLS | >200 | 2.8 | >71 |
| ED$_{50}$ (μM) FOR INHIBITING |  |  |  |

TABLE III-continued
COMPARISON OF EFFECTS OF FEAU AND FMAU IN MAMMALIAN CELLS

|  | FEAU | FMAU | FEAU/FMAU |
|---|---|---|---|
| THYMIDINE INCORPORATION INTO DNA |  |  |  |
| P-815 CELLS | 700 | 14.0 | 50 |
| L-1210 CELLS | 630 | 28.0 | 22 |
| RAT BONE MARROW CELLS | 3,700 | 8.9 | 415 |

TABLE IV
INCORPORATION OF [2-$^{14}$C] FEAU OR [2-$^{14}$C] FMAU INTO DNA OF MAMMALIAN CELLS INCORPORATION AT 10 μM (IN pMOLE/10$^6$ CELLS/HR)

| CELL LINE | FEAU | FMAU |
|---|---|---|
| L-1210 | NOT DETECTABLE* | 0.69 |
| VERO | NOT DETECTABLE* | 1.3 |
| HSV-1 INFECTED VERO CELLS | 0.48 | 3.4 |

*NOT DETECTABLE AT 100 μM

It is generally accepted that the selective anti-herpes activity of 2'-fluoro-arabinosylpyrimidine nucleosides is associated in large measure with their ability to be recognized as good substrates for HSV-specified thymidine kinase (TK), but not by the host TK (14, 15). As shown in Table V, FMAU is a good substrate (relative to thymidine) for cytosol and mitochondrial TK's derived from the HL-60 human cell line, as well as for HSV-1 and HSV-2 derived TKs. By contrast, FEAU is a very poor substrate for the host HL-60 derived TKs (13). These data are consistent with the recent report by Mansuri et al. (16) who showed that FEAU has a very low affinity for Vero cell TK (compared to thymidine) but a high affinity toward HSV-1 and HSV-2 encoded TK's. Their data also indicate that, in uninfected Vero cells, FEAU would be phosphorylated at a very low rate in the presence of thymidine.

These biochemical studies (10, 12–16) suggest that FEAU should be more selective in its antiviral activity and thus offer less host toxicity. In vivo experiments with mice (10, 13) show that both FMAU and FEAU are relatively nontoxic. However, FMAU is very neurotoxic in dogs (lethal dose 2.5 mg/kg/day, i.v.×5), while preliminary studies on FEAU in dogs at 50 mg/kg/day×10 show only moderate toxicity (lethal dose 100 mg/kg/day×10). As mentioned previously, FMAU exhibited dose-limiting CNS toxicity in patients with advanced cancer (7) at an intravenous dose of 0.8 mg/kg/day×5.

TABLE V
PERCENTAGE RATES OF PHOSPHORYLATION OF FEAU AND FMAU (RELATIVE TO THYMIDINE*) BY VARIOUS THYMIDINE KINASES

| ENZYME SOURCE | FEAU | FEAU |
|---|---|---|
| HL-60 CELLS | | |
| CYTOSOL TK | 0-2.1 | 81.7 |
| MITOCHONDRIAL TK | N/A | 219.0 |
| HSV-1 (STRAIN KOS) TK | 82.7 | 42.0 |
| HSV-2 (STRAIN 333) TK | 203.2 | 146.6 |

*THYMIDINE AT 400 μM

Comparative Studies in Monkeys Against Simian Varicella Virus

Studies at the Delta Regional Primate Research Center compared the activities of FEAU and FMAU in African green monkeys infected with simian varicella virus (SVV). As shown in Table VI, the three untreated controls exhibited marked viremia and died by day 11. Monkeys treated with FEAU at three dose levels (intravenous route) showed no apparent toxicity even at the higher dose of 30 mg/kg/day×10. Hematology tests and serum chemistries for all treated monkeys were normal and viremia (relative to the controls) was minimal even at the low dose of 3 mg/kg/day. While the control monkeys developed severe rash, none of the FEAU-treated monkeys developed rash at these drug levels. Further studies showed that a lower dose of 1 mg/kg/day prevented development of rash but did not reduce viremia in two of three monkeys. These data suggest that the minimal effective dose in this system for FEAU is about 1 mg/kg/day. Concurrent studies with FMAU showed it to be about 40-fold more potent against SVV with a minimal effective dose of about 0.04 mg/kg/day×10.

FEAU was also highly effective in the treatment of simian varicella virus by the oral route. Oral administration at dose levels of 10, 3 or 1 mg/kg/day×10 prevented rash (Table VII) reduced viremia significantly. Even at the 1 mg dose, rash was almost entirely prevented (two vesicles appeared on day 9, then promptly disappeared). Doses of 10 mg/kg/day×10 by the oral route were without any observed toxicity.

Thus, FEAU is shown to be a highly effective and selective antiviral in the treatment of SVV infection by both the intravenous and oral routes.

TABLE VI
EVALUATION OF FEAU IN TREATMENT OF SIMIAN VARICELLA VIRUS INFECTION IN THE AFRICAN GREEN MONKEY: EFFECT ON VIREMIA

| TREATMENT GROUP* | MONKEY NUMBER | VIREMIA** - MEAN PFU ON DAYS P.I. | | | | |
|---|---|---|---|---|---|---|
| | | 3 | 5 | 7 | 9 | 11 |
| CONTROL - H₂O | G029 | 1 | 140 | >400 | DEAD | |
| | G030 | 3 | 163 | >400 | >400 | DEAD |
| | G031 | 1 | 99 | >400 | DEAD | |
| FEAU - 30 MG/KG/DAY | G023 | 1 | 0 | 0 | 0 | 0 |
| | G024 | 2 | 0 | 0 | 0 | 0 |
| FEAU - 10 MG/KG/DAY | G025 | 1 | 14 | 5 | 0 | 0 |
| | G026 | 0 | 1 | 1 | 0 | 0 |
| FEAU 3 MG/KG/DAY | G027 | 1 | 8 | 0 | 0 | 0 |
| | G028 | 0 | 1 | 1 | 0 | 0 |

*TREATMENT WAS ADMINISTERED BY IV INJECTION TWICE DAILY BEGINNING 48 HOURS AFTER VIRUS INOCULATION AND CONTINUING FOR TEN DAYS
**VIREMIA WAS DETERMINED BY CULTURE OF LYMPHOCYTES COLLECTED FROM 3 ML OF HEPARINIZED BLOOD ON INDICATED DAYS POST-INFECTION (P.I.). THE MEAN PFU EXPRESSED IS THE AVERAGE NUMBER OF PLAQUES PRESENT IN TWO FLASK OF VERO CELL CO-CULTURES INOCULATED WITH EACH LYMPHOCYTE SUSPENSION.

TABLE VII
EVALUATION OF ORAL DOSAGE OF FEAU IN THE TREATMENT OF SIMIAN VARICELLA VIRUS INFECTION IN THE AFRICAN GREEN MONKEY: EFFECT ON RASH#

| TREATMENT GROUP* | MONKEY NUMBER | RASH - SEVERITY ON DAYS P.I. | | | | | | | |
|---|---|---|---|---|---|---|---|---|---|
| | | 6 | 7 | 8 | 9 | 10 | 11 | 12 | 14 |
| CONTROL - PBS | F644 | ± | 3+ | 4+ | 4+ | DEAD | | | |
| | G668 | — | — | ± | 2+ | 1+ | ± | ± | — |
| | G604 | — | ± | 3+ | 4+ | 4+ | 2+ | + | + |
| FEAU - 10 MG/KG/DAY | G249 | — | — | — | — | — | — | — | — |
| | G267 | — | — | — | — | — | — | — | — |
| | G264 | — | — | — | — | — | — | — | — |
| FEAU - 3 MG/KG/DAY | G665 | — | — | — | — | — | — | — | — |
| | G257 | — | — | — | — | — | — | — | — |
| | G268 | — | — | — | — | — | — | — | — |
| FEAU - 1 MG/KG/DAY | G269 | — | — | — | — | — | — | — | — |
| | G270 | — | — | — | — | — | — | — | — |
| | G274 | — | — | — | ± | — | — | — | — |

*TREATMENT WAS ADMINISTERED BY STOMACH TUBE TWICE DAILY BEGINNING 48 HOURS AFTER VIRUS INOCULATION AND CONTINUING FOR TEN DAYS.
SEVERITY OF RASH WAS GRADED ON A SCALE OF ± TO 4+. A ± RASH WAS SCORED WHEN SEVERAL VESICLES WERE OBSERVED WHILE A 4+ RASH INDICATED THE WIDESPREAD DISTRIBUTION OF RASH OVER THE BODY SURFACE.

In view of (a) the in vitro activity (15, 17) of FIAC and FMAU against varicella zoster virus (VZV, a member of the human herpes virus group); (b) the reported efficacy of FIAC for the treatment of varicella zoster virus in Phase 2 trials in immunosuppressed patients (6); and (c) the in vivo activities of FMAU and FEAU against simian varicella virus described herein and elsewhere (18), one may expect that FEAU will also exhibit significant selective activity against VZV in humans.

EXAMPLE 2

Comparative Antihepatitis Virus Studies in Woodchucks

In this example, FEAU and FMAU were evaluated against woodchuck hepatitis virus (WHV) in chronically-infected woodchucks (an animal model of choice for evaluation of potential antihepatitis B virus agents in humans). FEAU inhibits WHV replication at 2 and 0.2 mg/kg/day×10 in all animals tested. The inhibitory effect was immediate, non-toxic and long-lasting. Preliminary studies indicated that FEAU is also effective against WHV when given by the oral route. FMAU also produced immediate inhibitory effects against WHV replication at doses of 2 and 0.2 mg/kg/day×5; however, unacceptable toxicities were observed with FMAU at these dosages.

Hepatitis B virus (HBV), a member of the Hepa-DNA viruses, causes acute and chronic hepatitis in humans. It is estimated that about 200 million people are carriers of this virus. HBV may be the primary causative agent of hepatocellular carcinoma (19). Hepa-DNA viruses have also been discovered in other animals such as the woodchuck (Marmota Monax). The close structural and clinical pathological similar-ities, including nucleic acid homology (20), noted between woodchuck hepatitis virus (WHV) and HBV suggest that the woodchuck represents a useful model for studying persistent hepatitis virus infections as well as their relationship to the development of liver cancer (21). Like HBV, the woodchuck hepatitis virus elaborates a very similar DNA polymerase for its replication and integration. Potential anti-HBV agents may be detected by their inhibition of endogenous WHV or HBV DNA polymerase obtained from sera prepared from chronic-carrier woodchucks and from an immunosuppressed patients positive for the hepatitis B surface antigen. Such studies were undertaken at the Hepatitis Virus Unit, INSERM, Lyon, France, to measure the inhibitory effects of certain nucleoside triphosphates on these endogenous viral DNA polymerases.

In a series of assays (22, 23), the relative sensitivities of HBV and WHV DNA polymerases to several nucleoside triphosphates were determined (Table VIII). Of the six nucleoside triphosphates examined, FMAU was the most efficient inhibitor of both HBV and WHV DNA polymerases, followed closely by FIAC. Moreover, the potencies ($ID_{50}$'s) of each of these six triphosphates against HBV or WHV DNA polymerases, though not identical, were rather close. More important, the orders of potency as inhibitors of these viral DNA polymerases were identical. These results attest further to the striking similarities between HBV and WHV and point to the validity of the woodchuck as an animal model of choice for the in vivo evaluation of potential antihepatitis B virus agents (23).

Figure 2B:
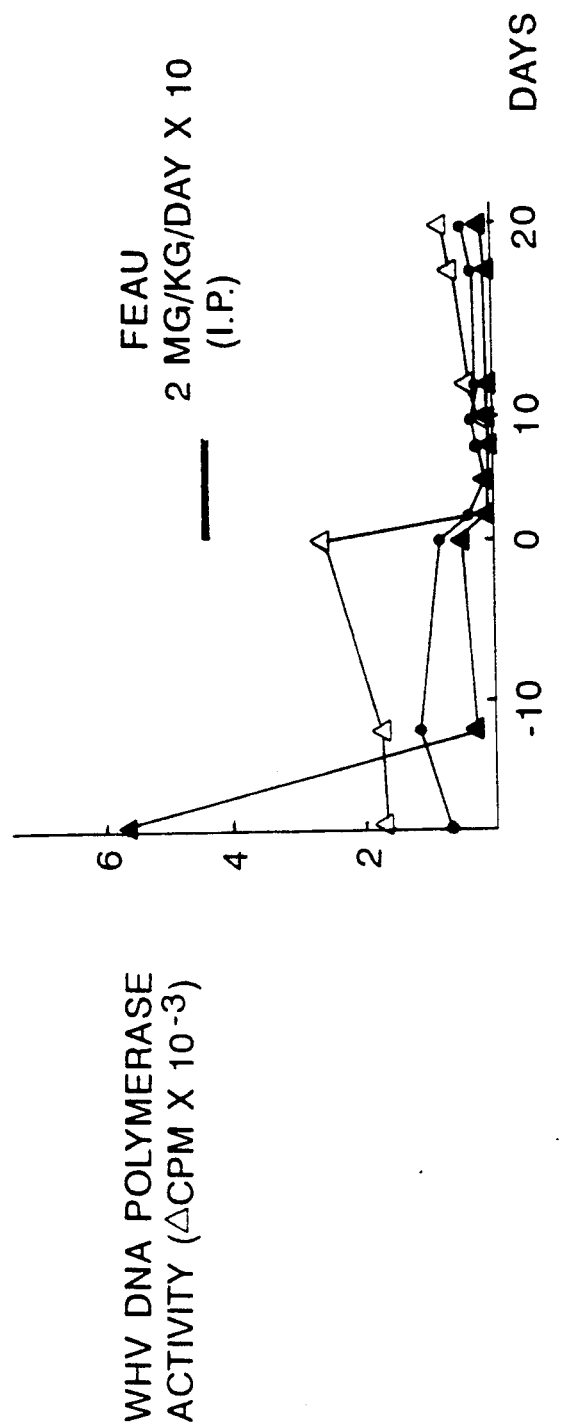
Figure 3B:
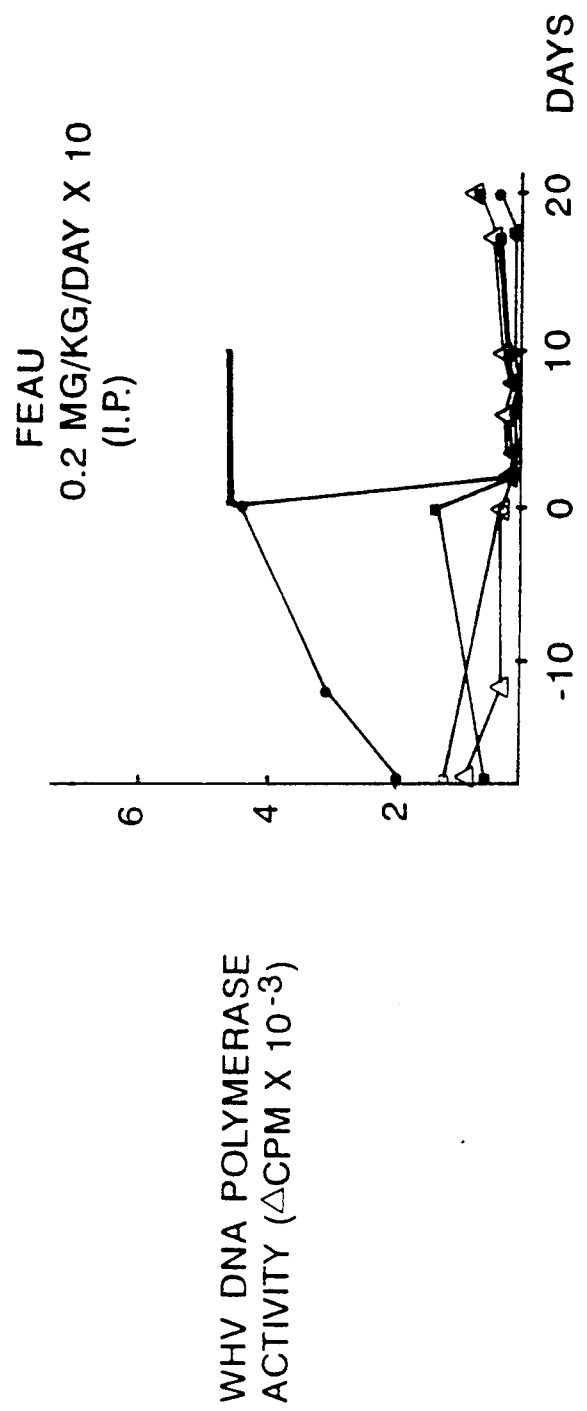
FIG. 3 is a comparison of the inhibition of WHV replication in woodchucks treated with FMAU (FIG. 3A) and FEAU (FIG. 3B) at lower doses.
Figure 4A:
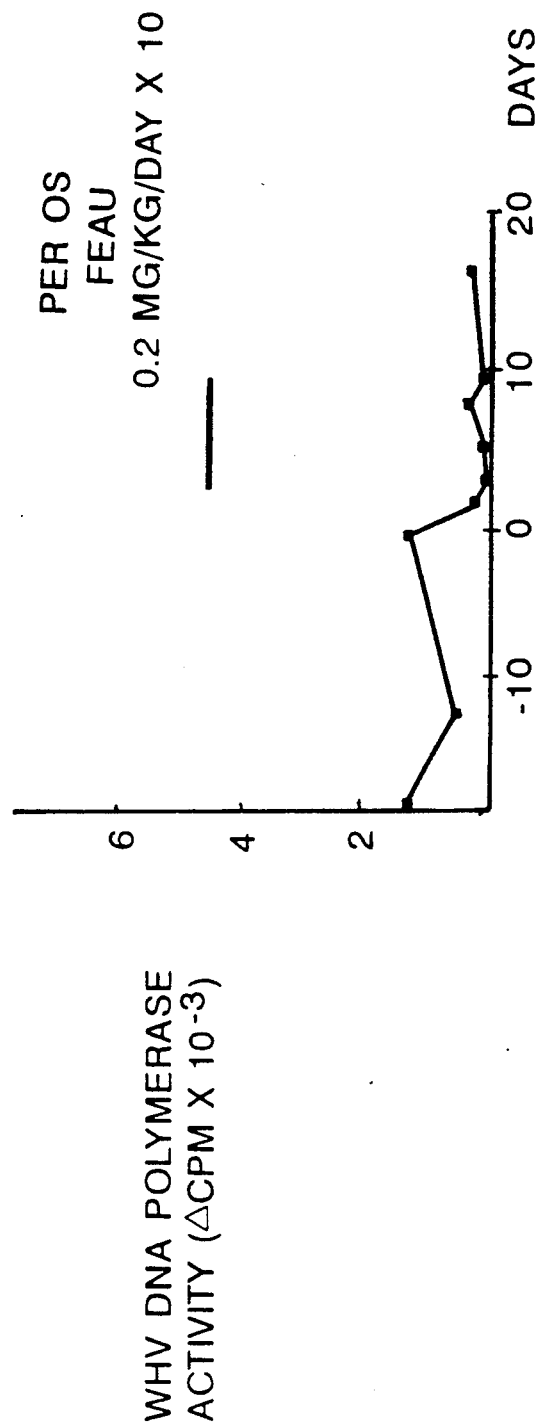
FIG. 4 illustrates inhibition of WHV replication in woodchucks by FEAU administered orally (FIG. 4A) versus controls (FIG. 4B).
Figure 4B:
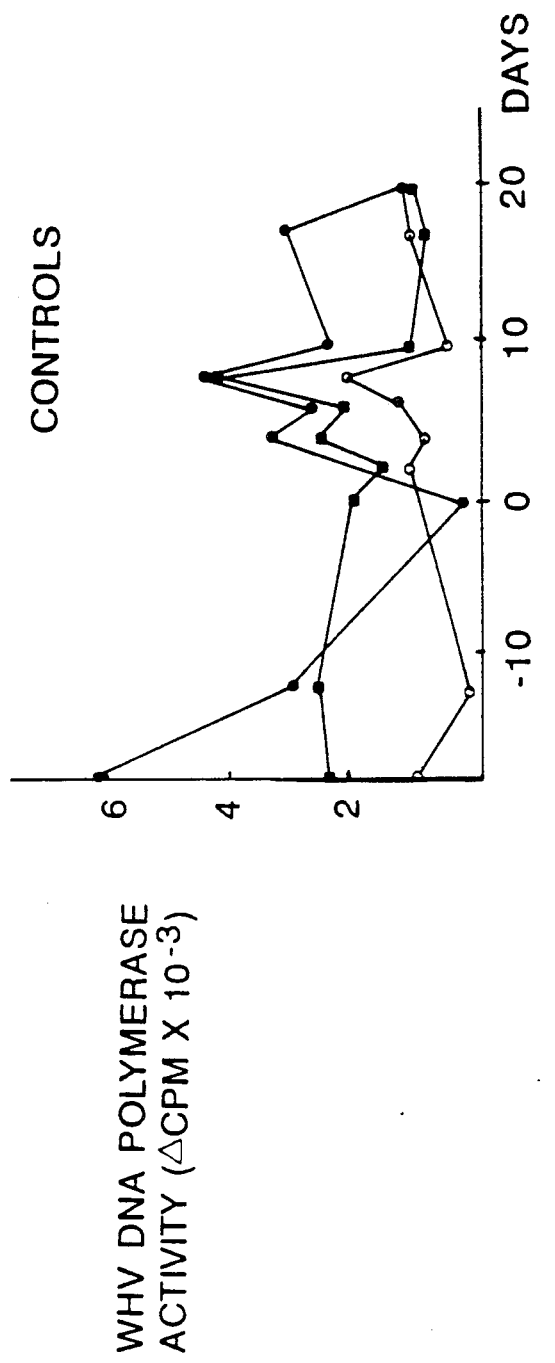

Studies were then undertaken to evaluate FMAU and FEAU in this animal model using woodchucks naturally chronically-infected with woodchuck hepatitis virus (24). It was assumed that these nucleosides would be anabolized to their nucleoside triphosphates within the animal. WHV replication was measured periodically by the endogenous DNA polymerase activity and by the detection of WHV DNA by the dot-blot hybridization assay. The viral DNA polymerase activities of untreated woodchucks are given in FIG. 1. Three different dosages of FMAU and FEAU were investigated. FMAU at 2 mg/kg/day×5, (given intraperitoneally beginning at day 0), produced marked inhibition of WHV replication as shown by the complete suppression of WHV DNA polymerase activity (FIG. 2A). However, at this dose, severe CNS toxicity was observed which was eventually lethal. FEAU administered i.p. at 2 mg/kg/day×10 also produced almost immediate suppression of WHV replication and did not exhibit any toxic effects (FIG. 2B). At 0.2 mg/kg/day, FMAU (given×5) and FEAU (given X 10) were equally effective in suppressing viral replication (FIGS. 3A and 3B). At this dose, FMAU exhibited a less severe and delayed toxicity, whereas FEAU was again nontoxic. Even at doses of 0.04 mg/kg/day×10, FEAU still exerted a somewhat diminished anti-WHV effect. A preliminary study with one woodchuck given FEAU by oral administration at a dose of 0.2 mg/kg/day×10 gave significant suppression of WHV replication, again without any observed toxicity (FIG. 4A).

TABLE VIII

COMPARATIVE INHIBITORY ACTIVITIES OF NUCLEOSIDE TRIPHOSPHATE ANALOGS ON DNA POLYMERASES OF HUMAN HEPATITIS VIRUS (HBV) AND WOODCHUCK HEPATITIS VIRUS (WHV)

| NUCLEOSIDE TRIPHOSPHATE INHIBITOR | $ID_{50}$ (μM)* | |
|---|---|---|
| | HBV DNA POLYMERASE | WHV DNA POLYMERASE |
| FMAU-TP | 0.025 | 0.05 |
| FIAC-TP | 0.05 | 0.10 |
| BVDU-TP | 0.25 | 0.30 |
| ARA T-TP | 0.30 | 0.40 |
| ACV-TP | 0.90 | 0.70 |
| ARA C-TP | 1.10 | 1.20 |

*$ID_{50}$ = CONCENTRATION OF INHIBITOR GIVING A 50% INHIBITION OF DNA POLYMERASE ACTIVITY.

After cessation of drug administrtion, the inhibitory activity of FEAU at 0.2 or 2 mg doses remained significant over a six-week period while returning slowly to pretreatment levels. FEAU inhibition of WHV replication was almost immediate and was markedly more sustained than is the case with other antivirals such as 6-deoxy-acyclovir, DHPG, or Ara-AMP. These latter drugs also diminished WHV DNA polymerase levels, but these soon rebounded to pretreatment levels after cesation of drug administration. In contrast to previous results obtained with FMAU and FIAC (where lethal toxicity was demonstrated), only about 10% weight loss was observed following FEAU treatment (24).

The observed efficacy of FEAU against woodchuck hepatitis virus replication at these low doses was quite surprising. On the basis of the in vitro studies on herpes simplex viruses (9, 10), the in vivo studies on the herpes encephalitis model in mice (10), and the simian varicella virus studies in the African green monkey reported herein, one would have expected that FEAU would be much less potent than FMAU. The data suggest that FEAU may be an effective agent clinically against hepatitis B virus. On the basis of its potency and selectivity, it appears to be the most promising of the nucleoside analogs tested thus far.

EXAMPLE 3

In accordance with the procedures of Example 2, the FEAU inhibition of WHV replication was further studied at different doses administered orally to woodchucks through stomach tubes. Two groups of woodchucks with different initial WHV replication values were examined.

A. High Replication

Seven woodchucks with high WHV replication were tested. High replication was defined as over 1000 counts per minute of DNA polymerase activity, and the mean replication was 1600. Two of these woodchucks were maintained as controls, and with slight fluctuations, exhibited the same WHV replication during the 60 days of the experiment.

The remaining five woodchucks were treated orally with 0.2 mg FEAU/kg/day. By the twenty-third day, all of these woodchucks had lowered replication values. However, four of the five were still above the normal level, defined as 50 counts per minute of DNA polymerase activity. Therefore, on day 24, the dosage of these four was increased to 1 mg FEAU/kg/day while the fifth was maintained at 0.2 mg FEAU/kg/day. By day 60, the replication was completely inhibited in all 5 animals with no toxic side effects.

B. Low Replication

Seven woodchucks with low WHV replication were tested. Low replication was defined as lower than 1000 counts per minute of DNA polymerase activity, and the mean replication was 600-800. Two of these woodchucks were maintained as controls, and with slight fluctuations, exhibited the same WHV replication during the 60 days of the experiment.

The remaining five woodchucks were treated orally with 0.04 mg FEAU/kg/day. By the twenty-third day, all of these woodchucks had lowered replication values. However, two of the five were still above the normal level. Therefore, on day 24, the dosage of these two was increased to 0.2 mg FEAU/kg/day while the remaining three were maintained at 0.04 mg FEAU/kg/day. By day 60, the replication was completely inhibited in all 5 animals with no toxic side effects.

EXAMPLE 4

A. Antiviral drugs

FIAC, FMAU and FEAU were synthesized at the laboratory of the organic chemistry of the Memorial Sloan Kettering Cancer Center. FIAC was dissolved at 250 mg in 1N HCl then diluted at indicated concentrations in phosphate buffered saline. FMAU and FEAU were dissolved in sterile distilled water.

Ara AMP was provided by the Warner Lambert Company, Parke Davis (Detroit, Mich.). The drug was dissolved in sterile distilled water at a concentration of 5 mg/ml.

B. Woodchucks and experimental follow up

Woodchucks (Marmota monax) chronically infected by WHV were obtained from our breeding colony initially established from animals imported from Pennsylvania (Cocaline Woodchuck Farms, Reinholds, Pennsylvania). All animals were kept indoors (10°-25°) in separate cages, fed with rat chow and water ad libitum. Before experimentation, all animals as a routine in the colony were bimonthly tested for WHV serum markers providing therefore a valuable base line of WHV replication prior to this study. During therapy, all animals involved were bled every 3 days then every fifteen days for 2 months after and monthly thereafter during a follow up period of 6 months.

C. Selection of woodchucks for the study

For these studies, 46 WHV chronic carrier woodchucks were used in 3 independent in vivo experiments. According to the WHV replication level, the animals were divided in two groups: one with high replication level as measured by the WHV endogenous DNA polymerase assay (>1000 cpm of $^3$H dTTP incorporated for 50 $\mu$l of serum), and one with middle (500-1000 cpm) or low (<500 cpm) level of replication. Both sexes were equally represented in the two groups of animals but the ages of the woodchucks were different. Carrier animals high replicators of WHV were generally young animals (mean age 1-2 years). By contrast moderate and especially low replicators were old woodchucks (3-4 years old). In many cases it was observed that low level of WHV replication is associated with the establishment and the progression of liver cancer which can be detected, as in man, by monitoring the levels of serum $\alpha$ focto-protein and confirming by histologic observations. In the subject colony, like in other centers, 50% of chronic carrier animals develop cancer after 2 years of age and 100% at the age of 4 years.

D. Treatment Protocol

In the first experiments FIGS. 5B through 5E, all drugs were given by the intraperitoneal route (IP) in two daily doses (every 2 h). FIAC was used at a dosage of 20 mg/kg/day for 7 days FIG. 5C and ara AMP at a dosage of 20 mg/kg/d for 14 days FIG. 5D. FMAU was given at 0.2, 0.8 and 2 mg/kg/day for 7 days FIG. 5B while FEAU was given at dosage of 0.04, 0.2 and 2 mg/kg/day for 10 days FIG. 5E.

Figure 6A:
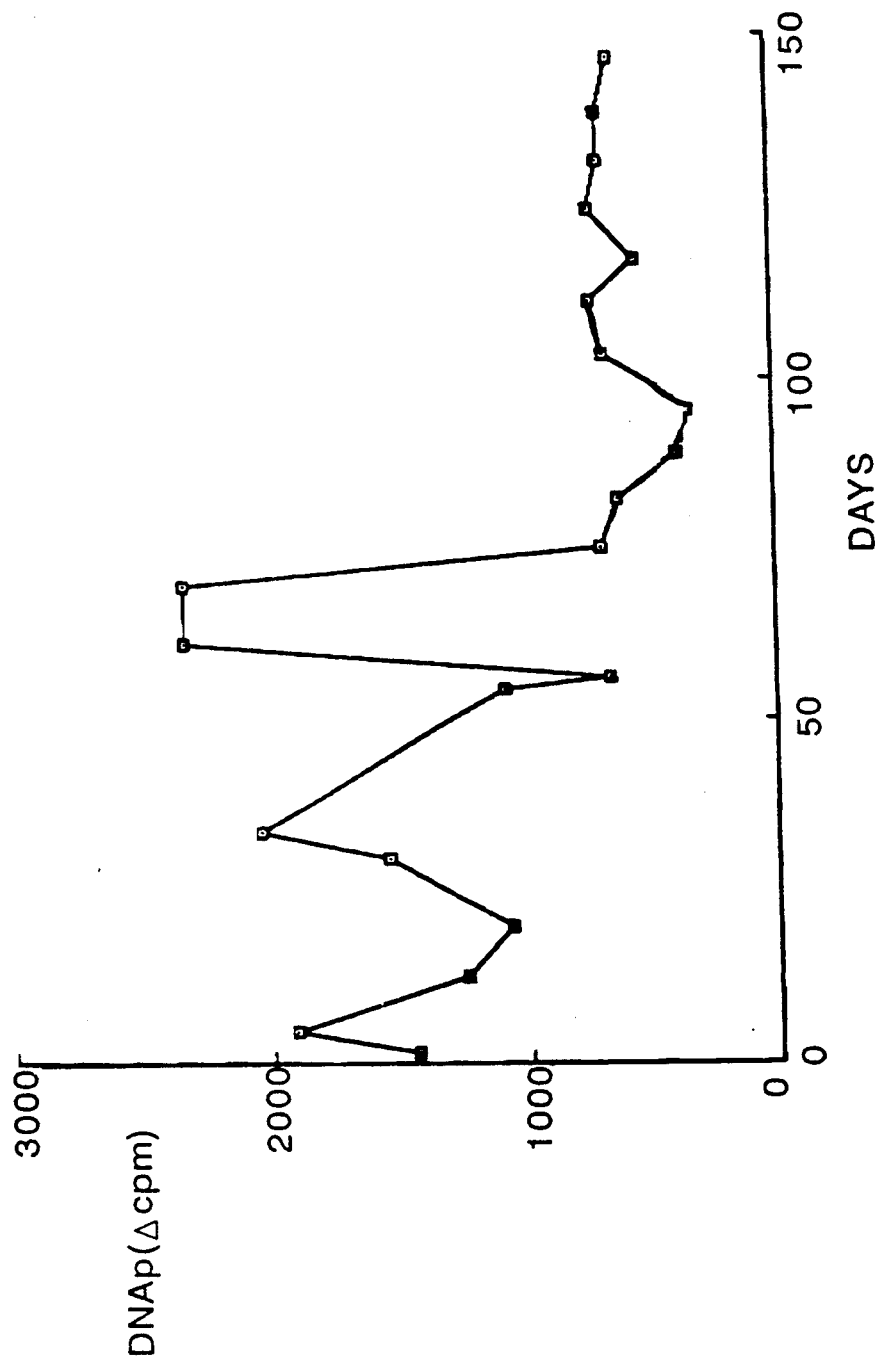
FIGS. 6A and 6B illustrate the effect of FEAU in prolonged oral administration:
6(A)=control
6(B)=treated.
Figure 6B:
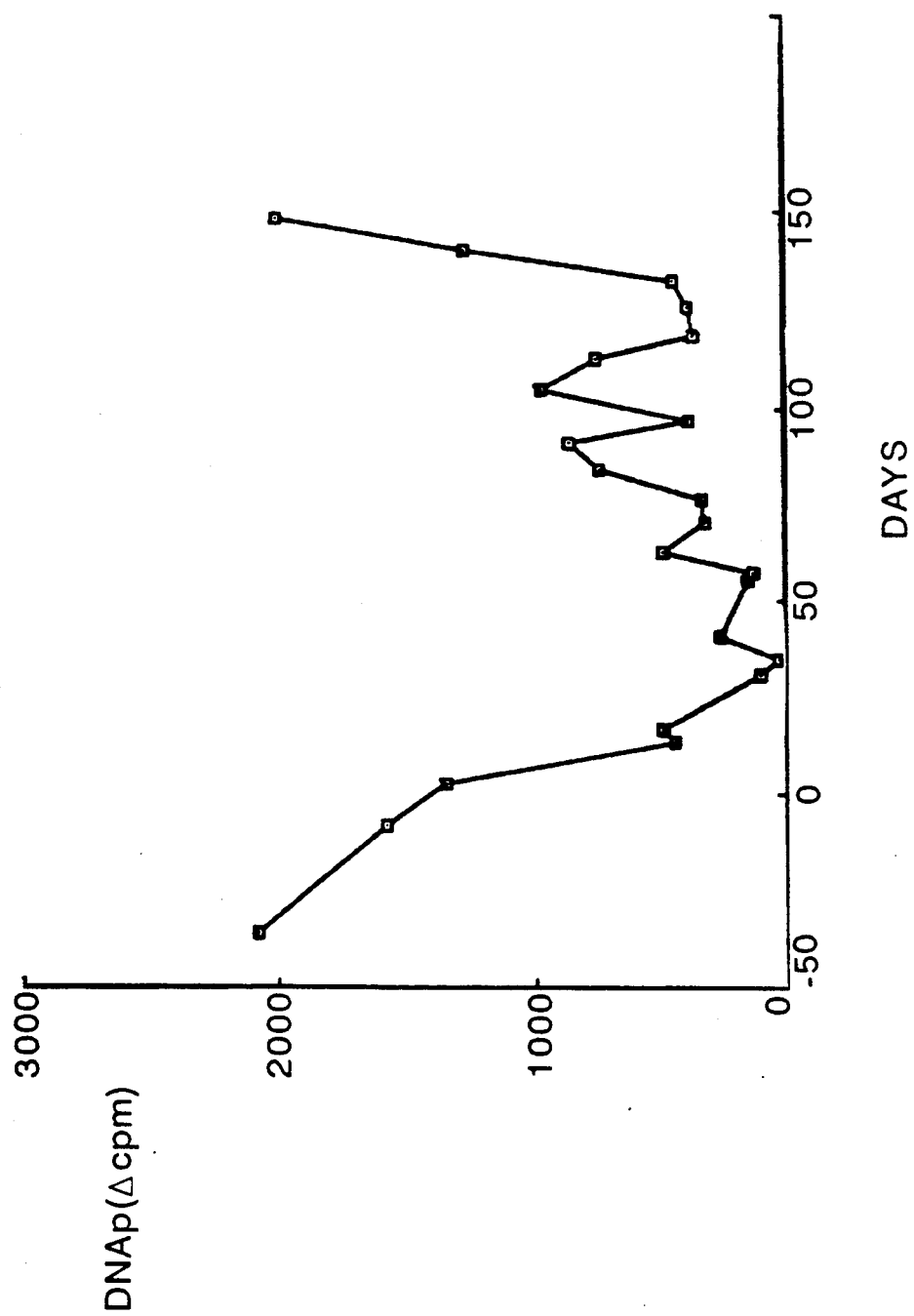

In another experiment, FEAU was given orally at 0.04 and 0.2 mg/kg/day. After 22 days of treatment, the animal received either the same regiment if replication was inhibited or an increased dose up to 2 mg/kg/day for 37 days (FIG. 6B). After 50 days of rest, FEAU was reintroduced at 0.04 mg/kg/day for 20 days.

E. Detection of WHV replication

Serology

WHV serological markers (WHs and WHe antigens and anti WHs antibody) were detected as previously described.

DNA polymerase assay

WHV DNA polymerase activity was determined directly on 50 $\mu$l of serum samples as described by Hantz et al. (23). The phosphonoformic acid (PFA) inhibitable $^3$H dTTP incorporation was obtained by calculating the difference ($\Delta$ cpm) between the polymerase activity without PFA and with PFA. In some cases, the assay was performed on virus pelleted from serum by ultracentrifugation at 40,000 rpm for 2 h at 4° C. in a 50.3 Ti (Beckman) rotor to rule out any possibility of interference due to residual antiviral compounds.

Detection of WHV DNA

Serum was also tested for the presence of WHV DNA by the hybridization spot test as previously described. Briefly, 50 $\mu$l of serum was directly spotted on a nitrocellulose filter using a BRL hybridot manifold apparatus. After denaturation and neutralization, filters were hybridized. Hybridization using a cloned WHV DNA probe labelled with $\alpha^{32}$P dCTP by nick translation technique was performed.

In the experiment of prolonged oral FEAU administration, wedge liver biopsies were obtained from treated woodchucks under general anesthesia on the day prior to starting treatment and 2 days before the first cycle of treatment. To detect WHV in liver tissue, tissue was homogenized in TEN solution (Tris 10 mM, EDTA 1 mM, NaCl 100 mM) with proteinase K in the presence of 0.1% SDS. Proteins were removed by extraction with phenol and chloroform. Nucleic acids were precipitated with ethanol and stored at 20° C. DNA was electrophorized, transferred to nitrocellulose and hybridized as described above.

F. Results

In clinical trials in man, particularly with ara AMP, the treatment efficacy clearly depends on the level of HBV replication and best results are observed in individuals with lower HBV DNA levels. Thus, in the subject experiment, all treatment protocols included woodchucks of both groups in order to see if the efficacy of the tested antiviral compound was dependent on the level of viral replication. The development of hepatocellular carcinoma in some animals is considered as an independent event which only interferes in the long term follow up of treated animals because of death as a result of the progression of the tumor.

Effect of short-term therapy with FIAC, FMAU and FEAU by IP

Table IX summarizes the treatment protocol and results as depicted also in FIGS. 5A to 5E.

TABLE IX

TREATMENT PROTOCOL OF WHV CHRONICALLY INFECTED WOODCHUCKS WITH FIAC, FMAU, FEAU AND ara AMP BY IP

| COMPOUND | DOSE mg/kg/d | DURATION OF TREATMENT (days) | NUMBER OF TREATED ANIMALS |
|---|---|---|---|
| FIAC | 20 | 7 | 2 |
| FMAU | 2 | 6 | 4 |
| FMAU | 0.8 | 5 | 2 |
| FMAU | 0.2 | 5 | 2 |
| FEAU | 0.04 | 10 | 2 |
| FEAU | 0.2 | 10 | 2 |
| FEAU | 2 | 10 | 3 |
| ara AMP | 20 | 14 | 4 |
| Controls | | | 11 |

Figure 5A:
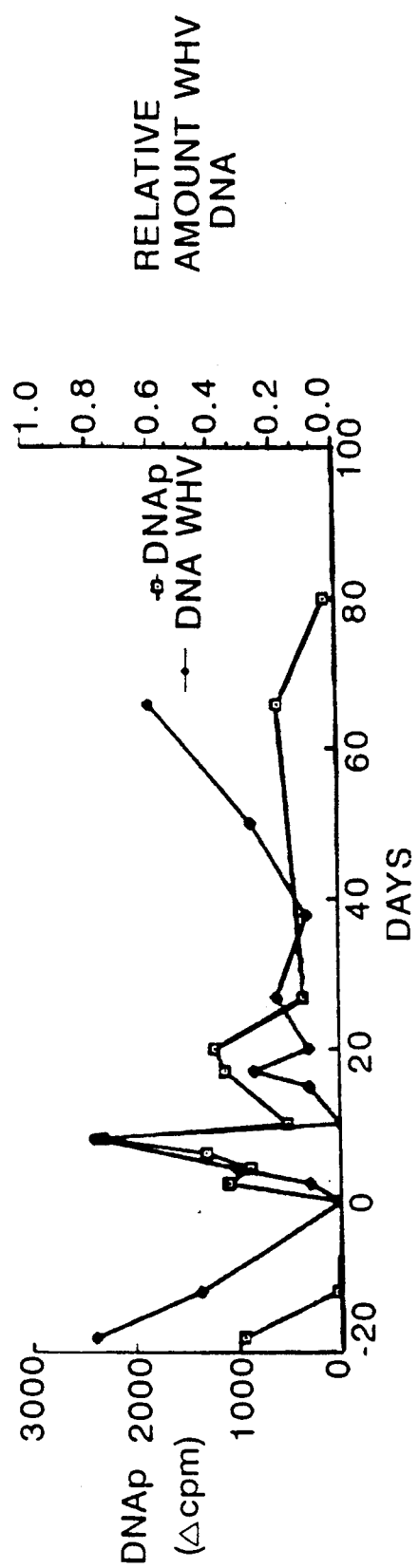
Figure 5B:
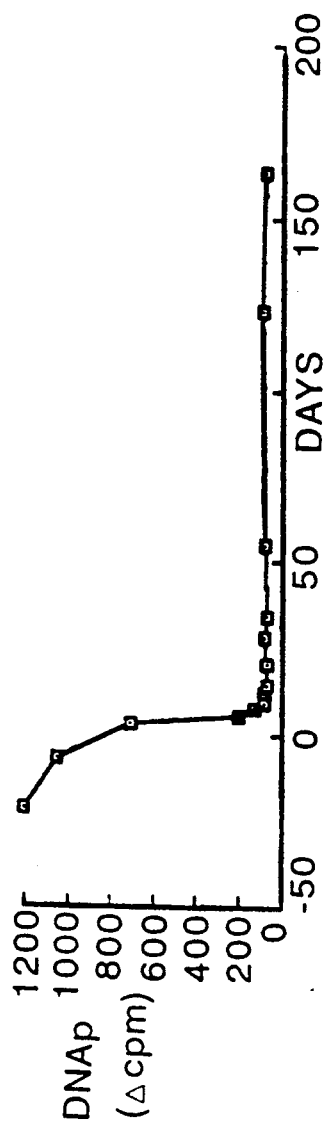
Figure 5C:
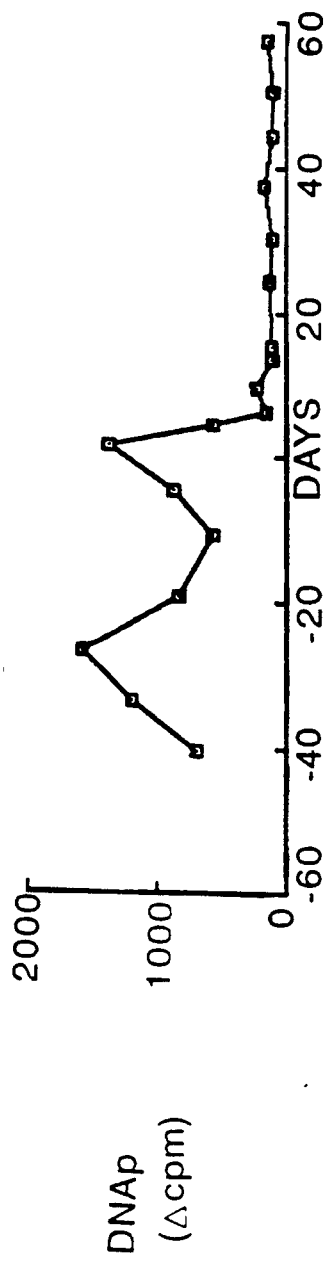

In all treated animals, FIAC and FMAU induced a dramatic and permanent inhibition of WHV replication. Indeed, WHV DNA polymerase could no longer be detected after the second day of treatment. The inhibition of WHV replication was confirmed by the hybridization spot test as shown in FIGS. 5B and 5C. Unfortunately, at the doses used, FIAC and FMAU appeared toxic. All treated animals showed a complete anorexia during treatment which lasted for more than 10 days afterwards. Three out of the 4 animals involved died: one died during treatment, the second 8 weeks later (FIAC) and the third 3 weeks later (FMAU). Only one animal survived. Early death was associated with central nervous system toxicity and later death with renal insufficiency. In a second experiment, the dose of FMAU was reduced to 0.8 and 0.2 mg/kg/d. As shown in FIG. 5B, even at 0.2 mg/kg/d, FMAU induced a dramatic decrease of WHV replication. The WHV DNA and DNA polymerase in serum could no longer be detected after 48 hours of treatment. However, as noted before, 2 months after cessation of treatment, one animal treated with 0.8 mg/kg/d died from renal insufficiency. The 3 other animals survived for at least 6 months after the end of treatment without reactivation of WHV replication. Despite the absence of WHV active replication, all animals remained WHs Ag positive.

Figure 5E:
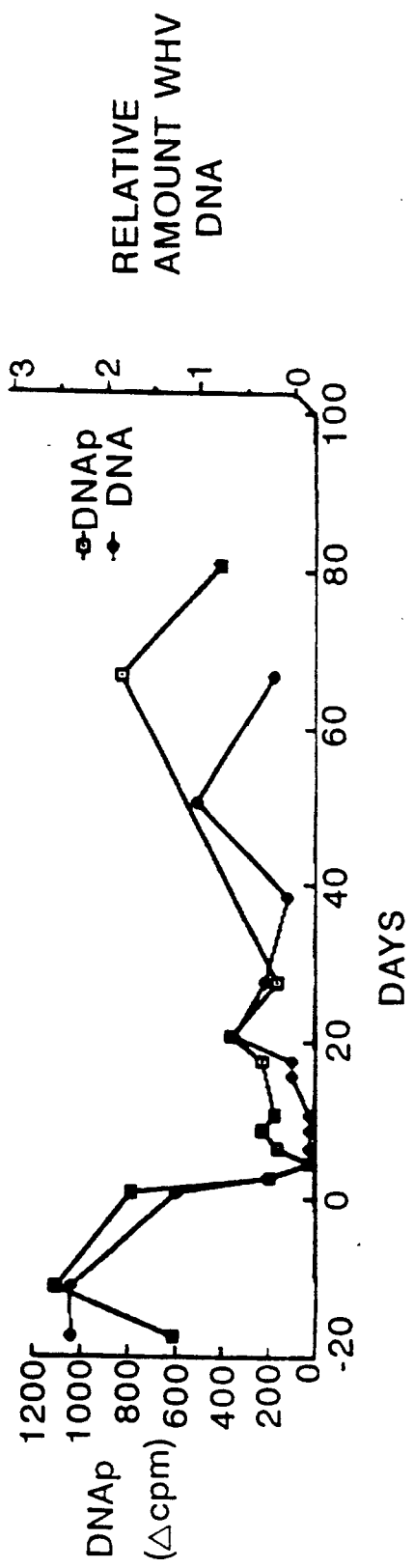

FEAU, like FMAU, induced a dramatic inhibition of WHV replication in serum. FEAU appeared to start to inhibit efficienctly WHV replication at 0.04 mg/kg/d and more completely at 0.2 mg/kg/d and 2 mg/kg/d. As shown in FIG. 5E, the inhibitory effect was immediate and long-lasting but not permanent. All animals survived the treatment protocol. Three animals with tumors, however, died at 3, 5 and 8 weeks after the end of treatment. These animals were low replicators 3 years old with elevated AFP for more than 9 months. During the same follow-up period, two low replicating old matched control animals also died from hepatocellular carcinoma.

With ara AMP (20 mg/kg/d) a significant decrease of the viral replication was observed during treatment. However, at the end of treatment, the WHV DNA polymerase level quickly increased again at a level similar or sometimes superior to the pretreatment level for all animals FIG. 5D.

Prolonged oral FEAU administration

In a further experiment, FEAU was given orally at doses lower than used in the previous experiment (Table X). In the first part of the study, FEAU was given at 0.04 mg/kg/d to 5 low replicators and at 0.2 mg/kg/d to 5 high replicators. FEAU induced a decrease of the viral replication in all treated animals. However after 22 days, the dose was increased whenever replication persisted. Two low replicators received 0.2 mg/kg/d (the 3 others remained at 0.04 mg/kg/d) and 3 high replicators received 1 mg/kg/d (2 remained at 0.2 mg/kg/d) during 37 days. The viral replication proceeded to reduce (DNAp<200 cpm) (FIG. 6B). Since replication resumed in all animals, after 50 days of rest FEAU was reintroduced at 0.04 mg/kg/d for 20 days. Diminution of WHV replication could be observed in treated animals which increased again at the end of treatment. Unfortunately, 4 old low replicators with tumors died before the end of treatment and 3 high replicators died 15 days, 1 month and 2 months after the end of the treatment. No apparent toxic effects were observed during the first course of treatment. But after the second cycle, animals developed anorexia with important loss of weight. At autopsy, animals presented pulmonary nodules which appeared as the likely consequence of FEAU accidentally pushed into the lung during gavage in some instances.

TABLE X

TREATMENT PROTOCOL OF WHV CARRIERS WITH FEAU BY ORAL ROUTE

| COMPOUND | DOSE mg/kg/d | DURATION OF TREATMENT | NUMBER OF TREATED ANIMALS |
|---|---|---|---|
| FEAU | 0.04 | 49 | 3 |
| FEAU | 0.20 | 49 | 2 |
| FEAU | 0.04 then 0.2 | 22 then 37 | 2 |
| FEAU | 0.2 then 1 | 22 then 37 | 3 |
| Control | | | 4 |

G. Discussion

By comparing the results obtained in vivo with the compounds, it appears that FIAC, FMAU and FEAU are far more effective than ara AMP. Indeed, the inhibitory effect was still present for several weeks after the end of treatment. FIAC and FMAU appear as the more potent inhibitors. Unfortunately, FIAC and FMAU exhibit toxic side effects even at low doses. On the contrary, FEAU appeared also very effective with fewer side effects than FMAU or FIAC. FEAU appears practically non-toxic when given IP for up to 2 months.

Since FEAU appeared as the most promising anti-HBV agent tested so far, the feasibility of using the oral route at low dose for a long period of time was studied. Indeed, FEAU is also effective by oral route but less than when administrated IP. Following the end of treatment, viral replication resumed and returned toward its pretreatment level. Unfortunately, FEAU also seemed to be associated with same side effect when given orally during a long time. This could in a large extent be explained by the following: i) for the oral administration, the animals must be crammed and some compounds could be passed in the pulmonary ducts causing pulmonary diseases; and ii) for the animals which hibernate and have particular metabolism, the drug may be metabolized differently or accumulated.

References

1. K. A. Watanabe, U. Reichman, K. Hirota, C. Lopez, J. J. Fox, J. Org. Chem. 22: 21–24 (1979).
2. J. J. Fox, C. Lopez, K. A. Watanabe in Medicinal Chemistry Advances (F. G. de las Heras, S. Vega, eds), Pergamon Press, Oxford, pp. 27–40 (1981).
3. T-C. Chou, A. Feinberg, A. J. Grant, P. Vidal, U. Reichman, K. A. Watanabe, J. J. Fox, Cancer Res. 41: 3336–3342 (1981).
4. J. A. Coderre, D. V. Santi, A. Matsuda, K. A. Watanabe, J. J. Fox, J. Med. Chem. 26: 1149–1152 (1983).
5. C. W. Young, R. Schneider, B. Leyland-Jones, D. Armstrong, C. Tan, C. Lopez, K. A. Watanabe, J. J. Fox, F. S. Philips, Cancer Res. 43: 5006–5009 (1983).
6. B. Leyland-Jones, H. Donnelly, S. Groshen, P. Myskowski, A. L. Donner, M. Fanucchi, J. J. Fox, J. Infectious Dis. 154: 430–436 (1986).
7. M. P. Fanucchi, B. Leyland-Jones, C. W. Young, J. H. Burchenal, K. A. Watanabe, J. J. Fox, Cancer Treatment Rep. 69: 55–59 (1985).
8. K. A. Watanabe, T-L. Su, U. Reichman, N. Greenberg, C. Lopez, J. J. Fox, J. Med. Chem. 27: 91–94 (1984).
9. M. E. Perlman, K. A. Watanabe, R. F. Schinazi, J. J. Fox, J. Med. Chem. 28: 741–748 (1985).
10. J. J. Fox, K. A. Watanabe, R. F. Schinazi, C. Lopez in Herpes Viruses and Virus Chemotherapy (R. Kano, A. Nakajima, eds.) Excerpta Medica, Amsterdam, pp. 53–56 (1985). Based upon proceedings of International Symposium on Pharmacological and Clinical Approaches to Herpes Viruses and Virus Chemotherapy presented in Oiso, Japan, September, 1984.
11. R. F. Schinazi, J. Peters, M. K. Sokol, A. J. Nahmias, Antimicrobial Agents Chemother 24: 95–103 (1983).
12. T-C. Chou, X-B. Kong, V. P. Potter, F. A. Schmid, J. J. Fox, K. A. Watanabe, M. Fanucchi, Proceedings of AACR 26: 333 (1985).
13. T-C. Chou, X-B. Kong, M. P. Fanucchi, Y-C. Cheng, K. Takahashi, K. A. Watanabe, J. J. Fox, Antimicrobial Agents Chemother (in press).
14. Y-C. Cheng, G. Dutschman, J. J. Fox, K. A. Watanabe, H. Machida, Antimicrobial Agents Chemother 20: 420–423 (1981).
15. C. Lopez, K. A. Watanabe, J. J. Fox, Antimicrobial Agents Chemother 17: 803–806 (1980).
16. M. M. Mansuri, I. Ghazzouli, M. S. Chen, H. G. Howel, P. R. Brodfuehrer, D. A. Benigni, J. C. Martin, J. Med. Chem. 30: 867–871 (1987).
17. H. Machida, A. Kuninaka, J. Yoshinao, Antimicrobial Agents Chemother 21: 358–361 (1982).
18. K. F. Soike, C. Cantrell, P. J. Gerone, Antimicrobial Agents Chemother 29: 20–25 (1986).
19. B. S. Blumberg, W. T. London in Clinical Management of Gastrointestinal Cancer (J. J. DeCosse, P. Sherlock, eds.) Martinus Nijhoff Publishers, Boston, pp. 77–91 (1984).
20. F. Galibert, T. V. Chen, E. Mandart, Proc. Natl. Acad. Sci. U.S.A. 78: 5315–5319 (1981).
21. B. S. Blumberg, Hum. Pathol. 12: 1107–1113 (1981).
22. O. Hantz, T. Ooka, L. Vitvitski, C. Pichoud, C. Trepo, Antimicrobial Agents Chemother 25: 242–246 (1984).
23. O. Hantz, H. S. Allaudeen, T. Ooka, E. De Clercq, C. Trepo, Antiviral Res. 4: 187–199 (1984).
24. I. Fourel, O. Hantz, K. A. Watanabe, J. J. Fox, C. Trepo, Abstr. Amer. Assoc. Study Liver Diseases, Cleveland, Ohio. (October 1987).

What is claimed is:

1. A method of treating a hepatitis virus infection in a subject, caused by a hepatitis virus selected from the group consisting of a Hepatitis B Virus and a Woodchuck Hepatitus Virus, which comprises administering to the subject from about 0.04 mg/kg body weight of the subject/day to about 2 mg/kg body weight of the subject/day of a compound having the structure:

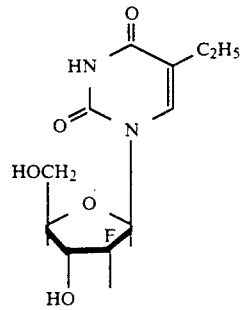

or a pharmaceutically acceptable salt thereof, effective to inhibit replication of the hepatitis virus in the subject and thereby treat the hepatitis virus infection.

2. The method of claim 1, wherein the administering comprises oral administration.

3. The method of claim 1, wherein the administering comprises intravenous administration.

4. The method of claim 1, wherein the subject is a human being.

* * * * *